(12) United States Patent
Morse

(10) Patent No.: US 8,102,735 B2
(45) Date of Patent: Jan. 24, 2012

(54) DOCKING STATION FOR MOUNTING AND PROGRAMMING MULTIFUNCTION TIMER DEVICE AND METHOD

(76) Inventor: Kevin C. Morse, Flint, MI (US)

( * ) Notice: Subject to any disclaimer, the term of this patent is extended or adjusted under 35 U.S.C. 154(b) by 432 days.

(21) Appl. No.: 12/387,980

(22) Filed: May 11, 2009

(65) Prior Publication Data

US 2009/0222130 A1    Sep. 3, 2009

Related U.S. Application Data

(60) Continuation-in-part of application No. 11/803,272, filed on May 14, 2007, now Pat. No. 7,532,544, which is a division of application No. 10/844,150, filed on May 12, 2004, now Pat. No. 7,236,428.

(51) Int. Cl.
*G04B 47/00* (2006.01)
*B65G 59/00* (2006.01)
*G06F 17/00* (2006.01)

(52) U.S. Cl. ......... 368/10; 221/2; 235/375; 235/462.01; 705/2

(58) Field of Classification Search .................... 368/10, 368/72–74, 88, 278; 221/2, 3, 15; 235/375, 235/385, 462.01; 705/2, 3
See application file for complete search history.

(56) References Cited

U.S. PATENT DOCUMENTS

| | | |
|---|---|---|
| 3,227,127 A | 1/1966 | Gayle |
| 4,207,992 A | 6/1980 | Brown |
| 4,360,125 A | 11/1982 | Martindale et al. |
| 4,419,016 A | 12/1983 | Zoltan |
| 4,437,579 A | 3/1984 | Obland |
| 4,483,626 A | 11/1984 | Noble |
| 4,504,153 A | 3/1985 | Schollmeyer et al. |
| 4,526,474 A | 7/1985 | Simon |
| 4,573,606 A | 3/1986 | Lewis et al. |
| 4,616,316 A | 10/1986 | Hanpeter et al. |
| 4,617,557 A | 10/1986 | Gordon |
| 4,674,651 A | 6/1987 | Scidmore et al. |
| 4,695,954 A | 9/1987 | Rose et al. |
| 4,725,997 A | 2/1988 | Urquhart et al. |
| 4,811,764 A | 3/1989 | McLaughlin |
| 4,849,948 A | 7/1989 | Davis et al. |
| 4,855,971 A | 8/1989 | Meisner et al. |
| 4,939,705 A | 7/1990 | Hamilton et al. |
| 4,953,745 A | 9/1990 | Rowlett et al. |
| 4,984,709 A | 1/1991 | Weinstein |

(Continued)

*Primary Examiner* — Vit Miska
(74) *Attorney, Agent, or Firm* — J. Gordon Lewis

(57) ABSTRACT

A multifunction timer device provides a time/date stamp on a dispensing container and includes a housing, a controller with a timer circuit contained in the housing, a display for displaying information from the timer circuit, and a multifunction input button. The input button is operable in predetermined sequences to select operating and display modes of the timer device. The input button can be operated to display an actual date or time, to display a current timer value, to select between count-up and count-down modes, and to increment a counter. An adhesive backing is provided for attaching the timer device to the container. A communications link is provided for interfacing the controller with an external programmer. A reset trigger is used to automatically reset the timer device when the object is moved in a particular way, such as when a lid is removed from a pill container. A docking station interconnected with a host data processing system encodes information read from a container label and writes scanned and stored data to the timer device while simultaneously mounting the timer device to the container.

25 Claims, 17 Drawing Sheets

U.S. PATENT DOCUMENTS

| | | |
|---|---|---|
| 5,088,056 A | 2/1992 | McIntosh et al. |
| 5,099,463 A | 3/1992 | Lloyd et al. |
| 5,181,189 A | 1/1993 | Hafner |
| 5,213,232 A | 5/1993 | Kraft et al. |
| 5,233,571 A | 8/1993 | Wirtschafter |
| 5,313,439 A | 5/1994 | Albeck |
| 5,347,453 A | 9/1994 | Maestre |
| 5,392,952 A | 2/1995 | Bowden |
| 5,408,443 A | 4/1995 | Weinberger |
| 5,472,113 A | 12/1995 | Shaw |
| 5,522,525 A | 6/1996 | McLaughlin et al. |
| 5,625,334 A | 4/1997 | Compton |
| 5,751,660 A | 5/1998 | Chappell |
| 5,751,661 A | 5/1998 | Walters |
| 5,774,865 A * | 6/1998 | Glynn ................................ 705/2 |
| 5,812,064 A * | 9/1998 | Barbour ....................... 340/5.91 |
| 5,852,590 A | 12/1998 | de la Huerga |
| 6,032,085 A * | 2/2000 | Laurent et al. ................ 700/242 |
| 6,150,942 A * | 11/2000 | O'Brien ..................... 340/573.1 |
| 6,294,999 B1 * | 9/2001 | Yarin et al. ................. 340/573.1 |
| 6,317,390 B1 | 11/2001 | Cardoza |
| 6,324,123 B1 | 11/2001 | Durso |
| 6,337,836 B1 | 1/2002 | Eidelson |
| 6,421,650 B1 * | 7/2002 | Goetz et al. ........................ 705/3 |
| 6,529,446 B1 | 3/2003 | de la Huerga |
| 6,545,592 B2 | 4/2003 | Weiner |
| 6,633,796 B1 | 10/2003 | Pool et al. |
| 6,667,936 B1 | 12/2003 | Ditzig |
| 6,710,703 B2 | 3/2004 | Huang |
| 6,845,064 B2 | 1/2005 | Hildebrandt |
| 6,877,658 B2 * | 4/2005 | Raistrick et al. ............... 235/385 |
| 7,844,361 B2 * | 11/2010 | Jean-Pierre ................... 700/236 |
| 2003/0198134 A1 | 10/2003 | Hildebrandt |
| 2005/0121407 A1 | 6/2005 | Hildebrandt |
| 2006/0218014 A1 * | 9/2006 | Walker et al. ..................... 705/3 |

* cited by examiner

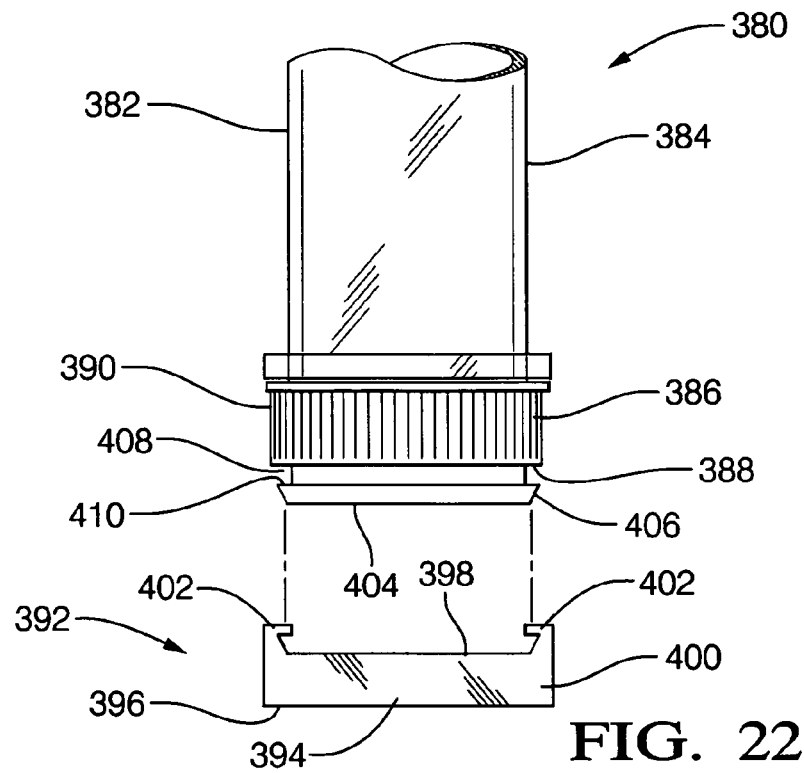
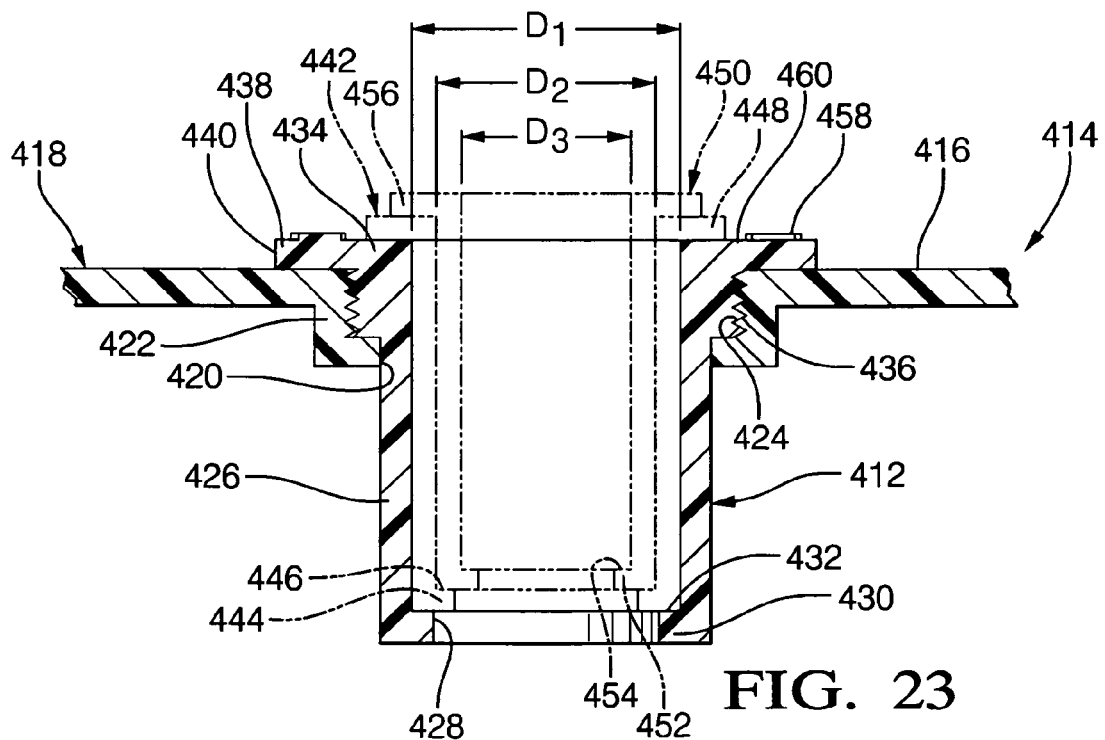

DOCKING STATION FOR MOUNTING AND PROGRAMMING MULTIFUNCTION TIMER DEVICE AND METHOD

RELATED APPLICATIONS

This application is a Continuation-In-Part application of U.S. Ser. No. 11/803,272 entitled "Multifunction Timer Device", filed 14 May 2007 now U.S. Pat. No. 7,532,544, which is a Divisional application U.S. Ser. No. 10/844,150 entitled "Multifunction Timer Device", filed 12 May 2004, now U.S. Pat. No. 7,236,428 B1, and owned by the common inventor/applicant.

TECHNICAL FIELD

The present invention relates generally to timer devices. In particular, the present invention relates to timer devices that can be attached to various objects and used to associate a particular time with the object. More particularly still, the present invention relates to apparatus for and methods of programming and mounting timer devices to associated dispensing containers.

BACKGROUND OF THE INVENTION

Many tasks in the home or in industry are time dependent. Food and pharmaceuticals are perishable. Equipment needs regular maintenance. With many of these time demands operating simultaneously (as they almost always do), it can be difficult to stay ahead of them and to prioritize those chores that need to be accomplished most urgently.

Some people use small, hand-written labels to mark the date that leftovers went into the freezer. Cars often carry small windshield tags reminding the driver of the next oil change date. Food carries "use by" dates. However, there remains a need for a multifunction device that consolidates all these applications and more using modern electronics to allow the device to be programmed for each particular application.

A variety of specific-use timer devices are known in the prior art for use with pharmaceuticals and pill containers. For example, U.S. Pat. No. 6,667,936 (Ditzig) shows a timer device that adheres to the top surface of a medicine bottle cap. The timer device includes an LCD and an electronic counting means that counts from 1 second up to 24 hours, at which time it flashes until reset. The device is automatically reset each time a user presses upon the top face (e.g., when opening the bottle).

U.S. Pat. No. 4,504,153 (Schollmeyer et al.) discloses a pharmacist-programmable timer device that can be built into or attached to a lid of a pill bottle. The device can be programmed (using an external programmer) to generate audible and visible prompting cues at intervals specified by the prescription instructions. The device is automatically reset in response to removal of the cap from the pill bottle or by use of a reset button.

U.S. Pat. No. 4,419,016 (Zoltan) discloses a timer device that can be attached to a cap of a pill container and reused with fresh containers. The device includes an LCD that identifies the time when the pill container was last opened and the elapsed time since the cap was last off. A "cap-on" sensor is used to reset each time the cap is taken off.

U.S. Pat. Nos. 6,317,390 (Cardoza), 5,751,661 (Walters), 6,545,592 (Weiner), 5,233,571 (Wirtschafter), and 4,939,705 (Hamilton et al.) each discloses a timer device built into the cap of a pill bottle. These timer devices have automatic resets that are activated when the cap is compressed or twisted.

U.S. Pat. No. 6,529,446 B1 (de la Huerga) discloses an interactive medication container that organizes one or more medication vials or containers. Each vial has a memory strip containing medication and prescription information. Each vial can also include a reminder unit that is attached to and portable with the individual vials. The console or reminder unit reads the information strip of the vial and communicated this information or interacts with the patient to remind them to take the medication.

Despite continuing major scientific advancements in both the medical and pharmaceutical industries, a principle cause of the rapid rise in health-care costs is the patients' failure to take medications their doctors have prescribed. This particular phenomenon, known as "non-compliance" or "non-adherence" is a little known fact that not only costs the nation billions a year, but also, like health-care costs in general, is growing steadily larger.

Systems, such as described by de la Huerga, can be useful in providing reminders to a patient to take their medications and to provide limited communication between the patient and his medical providers. However, known systems tend to be complex and expensive and, as a result, are not commercially practicable in large volume applications.

Accordingly, what is required is an extremely reliable and inexpensive system with maximum connectivity between the patient and his health-care professional, and which can be used by a patient or family member with no more than an intuitive or lay understanding of its operating principles.

SUMMARY OF THE INVENTION

An object of the present invention is to provide a multifunction timer device for associating particular tasks with particular times, which can be programmed simply and easily for use in a variety of applications.

Further objects of the present invention are to provide an inexpensive and reliable device for associating a time with an object; to provide a device that can be affixed to many different surfaces using an adhesive or other suitable means; and to provide a timer device that is compact in size while maintaining an easy to use interface.

It is a further object of the present invention to provide a timer device having a multifunction input button which is operable in predetermined sequences to change between a plurality of operating and display modes.

In order to accomplish these and other objects of the invention, a multifunction timer device is provided that includes a housing, a controller with a timer circuit contained in the housing, a display for displaying information from the timer circuit, and a multifunction input button. The input button is operable in predetermined sequences to select from among a plurality of operating and display modes of the timer device. The input button can be operated to display an actual date or time, a time of the last time/date of an action, to display a current timer value, to select between count-up and count-down modes, and to increment a counter. An adhesive backing is provided for attaching the timer device to an object. A communications link is provided for interfacing the controller with an external programmer. A reset trigger is used to reset the timer device when the object is moved in a particular way, such as when a lid is removed from a pill container.

According to a broad aspect of the present invention, a timer device is provided comprising a housing, a controller with a timer circuit contained in the housing, a display on the housing for displaying information from the timer circuit, and a multifunction input button. The input button is operable in a plurality of predetermined sequences to select from among a plurality of operating and display modes of the timer device.

According to another broad aspect of the present invention, a timer device for use with a container is provided, comprising: a housing adapted to be attached to a container; a controller with a timer circuit and a counter in the housing; a display on the housing for displaying information from the timer circuit; and a reset trigger having an adhesive strip for attaching the trigger to the container separate from the housing, whereby the counter of the timer circuit is automatically reset when the housing moves relative to the reset trigger upon opening the container.

According to another broad aspect of the present invention, a method of displaying a time/date stamp on an object is provided, comprising the steps of: attaching a timer device to the object, the timer device including a timer circuit having a plurality of operating modes and a display for displaying information from the timer circuit; and operating a multifunction input button on the timer device according to a predetermined sequence to select one of the operating modes for the timer circuit.

According to another broad aspect of the present invention, a docking station is provided for programming and mounting a multifunction timer device to a dispensing container. The docking station comprises a base portion which fixedly prepositions a multifunction timer device in alignment with an infrared light emitting diode (LED) for optical coupling there between. A platform portion is carried on said base portion and nestingly retains an end surface of a dispensing container in alignment with an exposed surface of said prepositioned multifunction timer device. The docking station functions to effect engagement between said container end surface and exposed timer surface. A scanner having a field of focus directed toward an outer peripheral surface of a dispensing container disposed on the platform portion operates to encode information imprinted thereon. Finally, a controller electrically interconnects the LED and scanner with a host data processing system and is operative to write selected data to the multifunction timer device via the LED optical coupling as a function of encoded information and related data stored in the host data processing system.

According to another aspect of the invention, the platform portion of the docking station includes a well for positioning dispensing containers, and the base portion includes a pocket for pre-positioning a multifunction timer device in axial alignment with the dispensing container. The platform is resiliently coupled to the base to enable manual displacement for precise interconnection of the timer with one end of the container. This arrangement provides simple, rapid application of a timer at a point-of-sale.

According to still another aspect of the invention, the platform borne well is reconfigurable to accommodate the use of multiple standard sized containers to maximize the docking station's utility.

According to yet another aspect of the invention, the platform portion of the docking station includes a plurality of wells for positioning dispensing containers of varying dimensions, and the base portion includes a single pocket for prepositioning a multifunction timer device in axial alignment with the dispensing container. The platform portion is rotationally displaceable with respect to the base portion for selective usage of one of the wells at a time. A locking mechanism is provided for releasable interconnecting the base and platform.

Numerous other objects of the present invention will be apparent to those skilled in this art from the following description wherein there is shown and described preferred embodiments of the present invention. Simply by way of illustration, some of the modes best suited to carry out the invention are described herein. As will be realized, the invention is capable of other different embodiments, and its several details are capable of modification in various obvious aspects without departing from the invention. Accordingly, the drawings and description should be regarded as illustrative in nature and not restrictive.

These and other features and advantages of this invention will become apparent upon reading the following specification, which, along with the drawings, describes preferred and alternative embodiments of the invention in detail.

BRIEF DESCRIPTION OF THE DRAWINGS

The present invention will now be described, by way of example, with reference to the accompanying drawings, in which:

FIG. 22, is a broken, exploded plan view of an inverted dispensing container with the end surface of the container closure member juxtaposed with an exposed surface of a multifunction timer device configured for self-engagement via cooperating engagement features;

FIG. 23, is a broken, cross-sectional view of the platform portion of an alternative embodiment of the invention including a reconfigurable well including several selectively removable inserts adapted for nestingly receiving dispensing containers of varying diameters and varying axial length.

Although the drawings represent embodiments of the present invention, the drawings are not necessarily to scale and certain features may be exaggerated in order to illustrate and explain the present invention. The exemplification set forth herein illustrates an embodiment of the invention, in one form, and such exemplifications are not to be construed as limiting the scope of the invention in any manner.

DESCRIPTION OF THE PREFERRED AND ALTERNATIVE EMBODIMENTS

A multifunction timer device according to preferred embodiments of the present invention will now be described in detail with reference to FIGS. 1 to 7 of the accompanying drawings.

Figure 1:
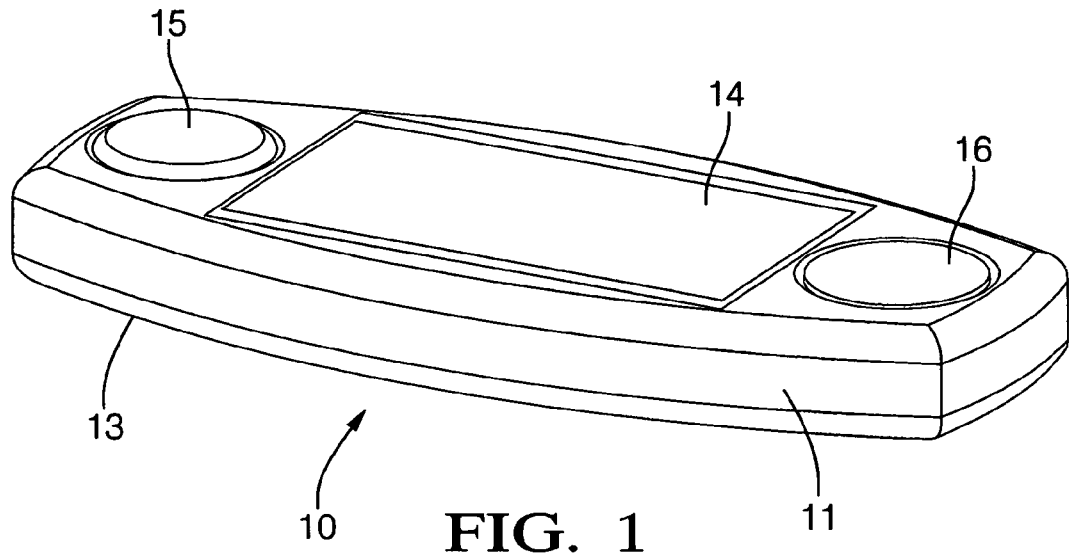
FIG. 1, is a perspective view of a multifunction timer device according to a first embodiment of the present invention.
Figure 2:
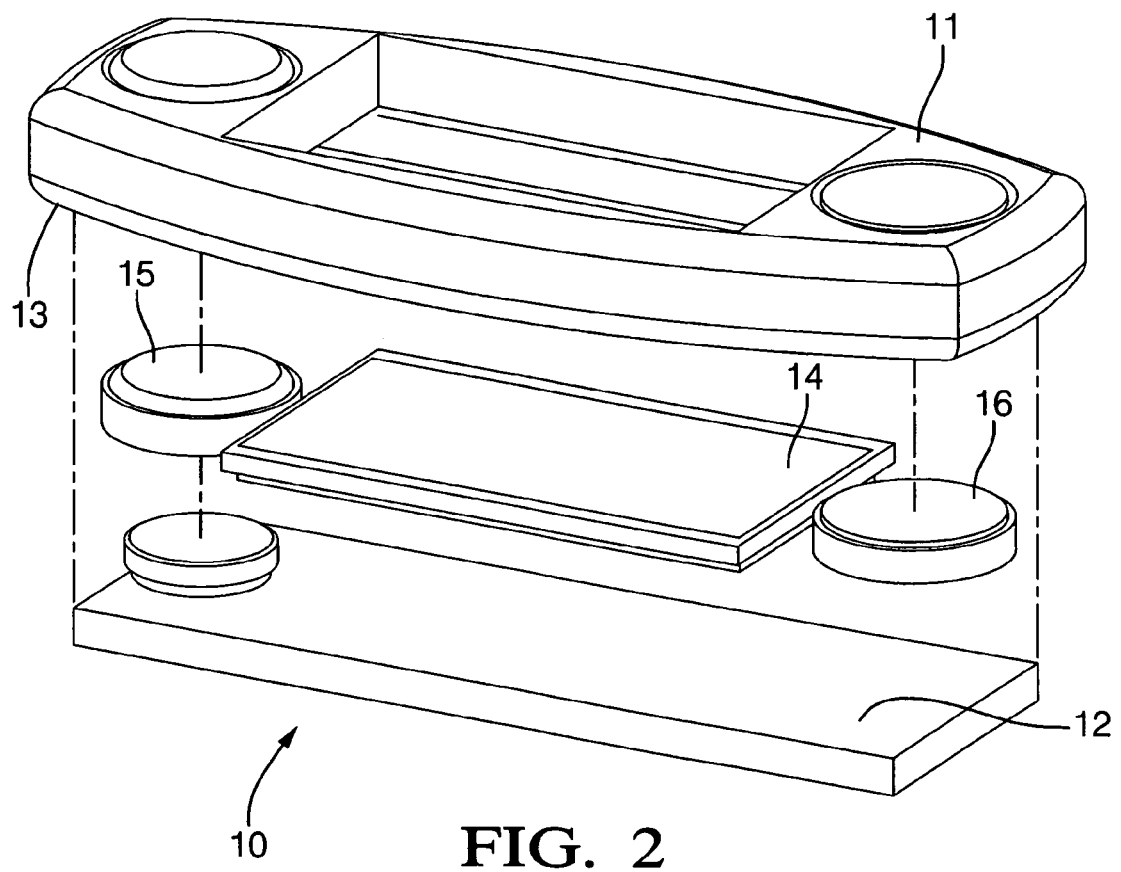
FIG. 2, is an exploded perspective view of the multifunction timer device shown in FIG. 1.

The multifunction timer device 10 according to a first embodiment of the present invention is shown in FIGS. 1 and 2 in assembled and disassembled conditions, respectively. The timer device 10 includes a housing 11 and various electronic components contained on a printed circuit board 12 contained within the housing 11. The housing 11 includes an adhesive strip 13 or other suitable fastening structure on a surface of its back side to secure the timer device 10 to an object, such as a food package, a pill container, a medical apparatus, or virtually any other object on which the user desires to associate a particular time with a particular task by fixing an electronic time/date stamp on the object.

The timer device 10 has a display interface 14 to display time information. The preferred display interface 14 is an LCD screen that allows precise time information to be conveyed to the user and is very compact and energy efficient. The timer information can be made to display only intermittently, and a backlit screen can be used to enhance viewing in low-light conditions. Other types of display interfaces include LED indicator lights, dials, and so forth.

Figure 5:
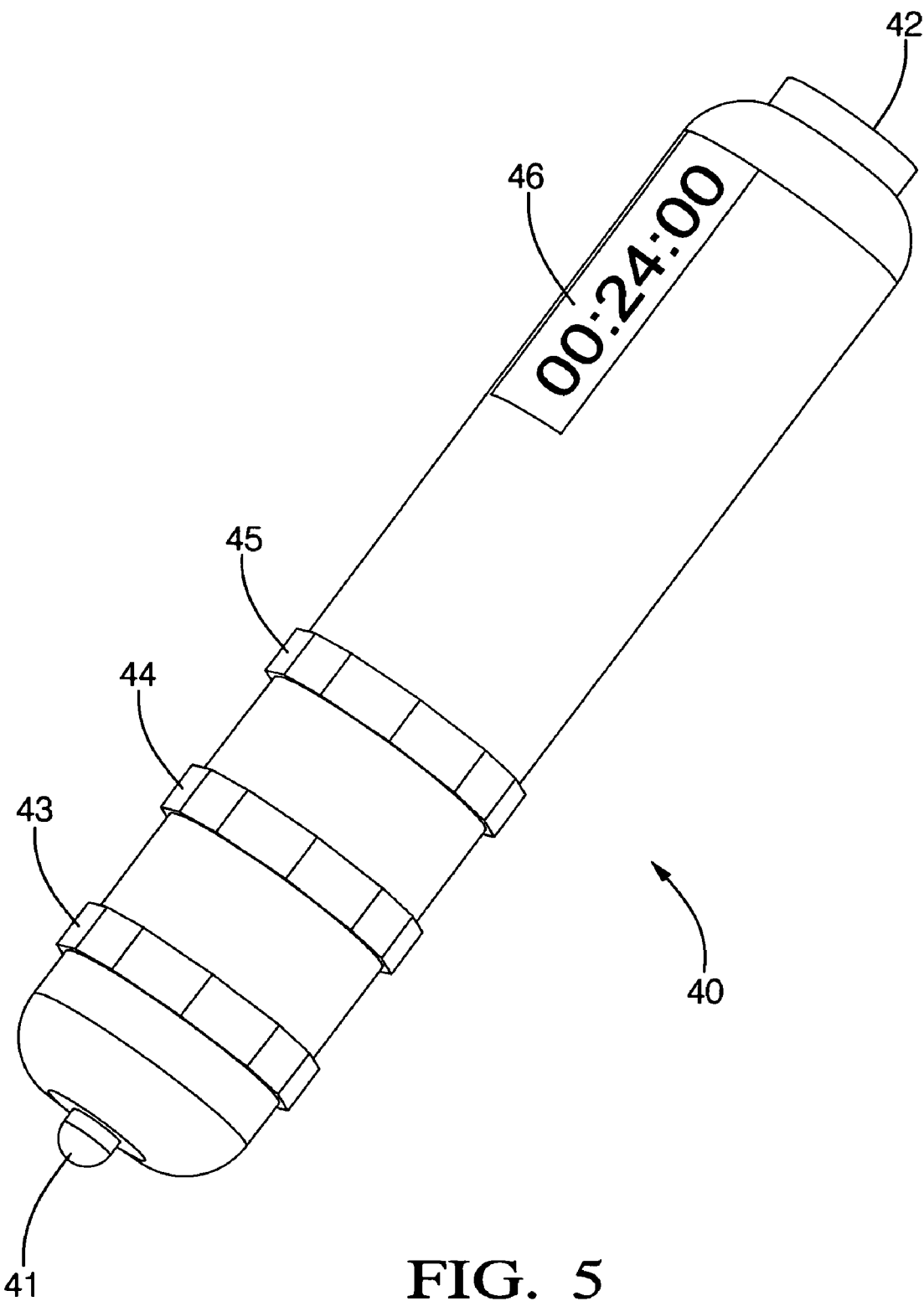
FIG. 5, is a perspective view of an external programmer used with the timer device of the present invention.

The timer device 10 also includes a multifunction input button 15 and a communications link 16, such as an infrared receiver, for interfacing with an external programmer 40 (shown in FIG. 5).

A timer device 20 according to a second embodiment of the invention will now be explained with reference to FIGS. 3 and 4 of the accompanying drawings. The timer device 20 is particularly suitable for attaching to the lid 21 of a pill container 22 or the like to provide an electronic time/date stamp for the pill container 22.

Figure 3:
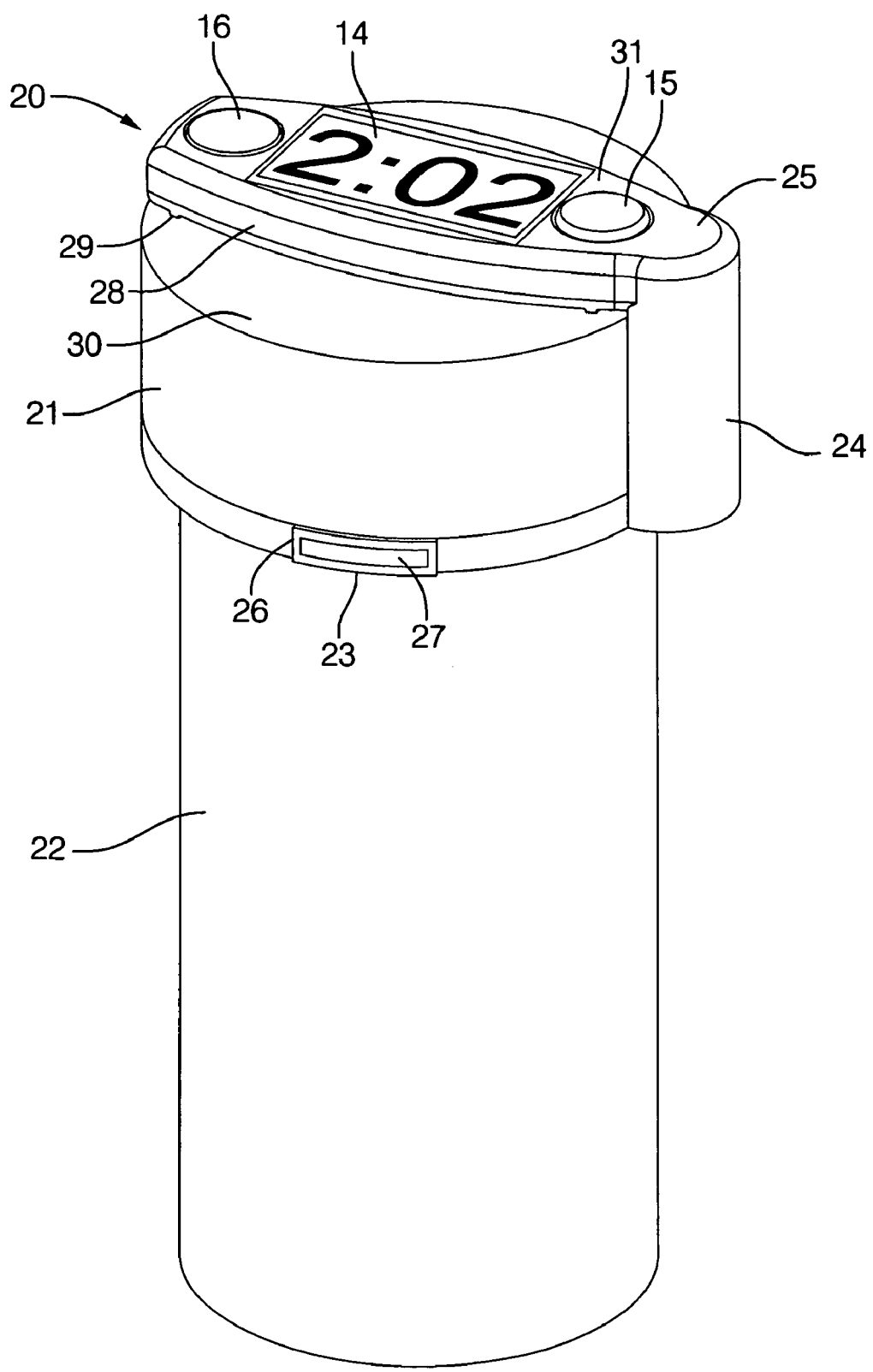
FIG. 3, is a perspective view of a timer device according to a second embodiment of the present invention attached to the lid of a pill container and having a reset trigger.
Figure 4:
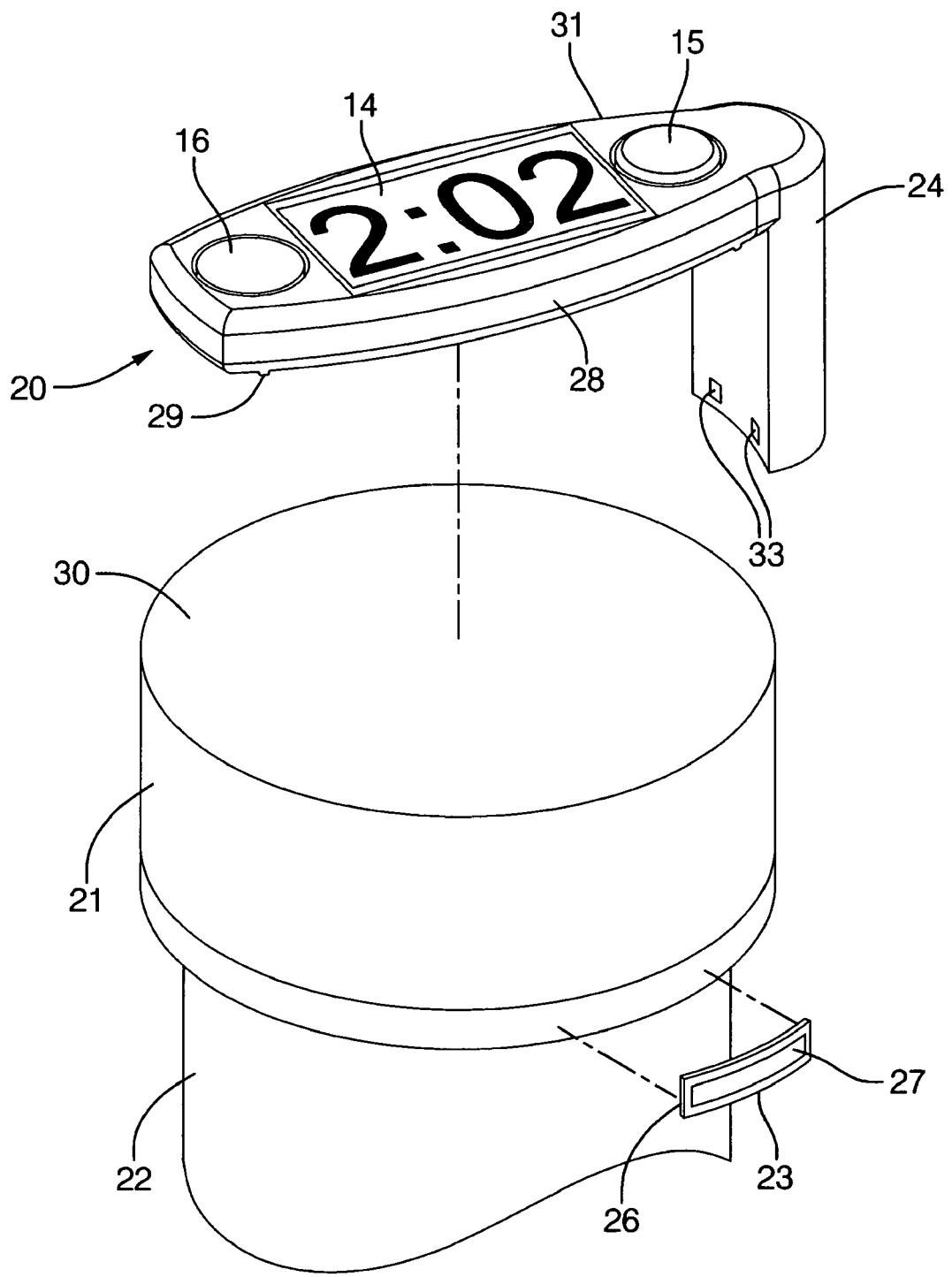
FIG. 4, is an exploded perspective view of the timer device, pill container, and reset trigger according to the second embodiment of the present invention.

The timer device 20 shown in FIGS. 3 and 4 includes many of the same basic features as the timer device 10 shown in FIGS. 1 and 2 and described above, and a further description of these same features will be omitted herein. The timer device 20 of the second embodiment differs from the timer device 10 of the first embodiment mainly in that it includes an automatic reset trigger 23 and an extended portion 24 of the housing 25 arranged to oppose the reset trigger 23.

The reset trigger 23 has an adhesive strip 26 or other suitable fastening means on its backside for attaching the trigger 23 to a sidewall of the container 22. The reset trigger has a conductive member 27 on its front side with a conductive surface facing outwardly from the container 22.

The housing 25 of the timer device 20 has a generally L-shaped configuration with a first leg 28 of the L shape corresponding generally to the housing 11 of the timer device 10 of the first embodiment. A first surface 29 on the backside of the first leg 28 is used for attaching the timer device 20 (e.g., using an adhesive) to a top surface 30 of the lid 21 of the container 22. The display interface 14 is arranged or exposed on a second surface 31 of the first leg opposite to the first surface 29. The extended portion 24 of the housing 25 provides the second leg of the L shape and extends downwardly from the first leg 28 to oppose the sidewall of the container 22. A pair of electrical contacts 33 are mounted to the second leg 24 on a side facing the sidewall of the container 22.

In one example embodiment, the electronics of the timer device 20 of the second embodiment include a counter for monitoring the number and/or frequency of times pills are taken from the container 22 based on when the lid 21 is removed. In another example embodiment, the electronics of the timer device 20 include a timer circuit in which the timer is reset each time a pill is taken (i.e., each time the lid 21 is removed). The pair of electrical contacts 33 are connected to a reset pin of the timer circuit within the timer device 20 such that the counter is incremented or the timer circuit is reset each time the pair of contacts 33 are moved into (or out of) contact with the exposed outer surfaces of the conductive member 27 as the lid 21 is twisted on the container 22.

FIG. 5 shows an external programmer 40 that can be used to communicate with the timer devices 10, 20 to set the initial timer mode, to set a start time for a countdown mode, and to imprint the current date and/or time into the memory of the timer device 10, 20. In the preferred embodiment, the programmer 40 communicates with the timer device 10, 20 through an infrared link. Since only a few packets of information need to be transmitted from the programmer 40 to the timer device 10, 20, the programmer 40 can communicate on a very low bandwidth, which provides a relatively forgiving communication link. Pointing the infrared link of the programmer 40 in the general direction of the timer device 10, 20 from within a few feet should be sufficient.

The communication link of the programmer 40 in the preferred embodiment is an infrared LED 41. The infrared LED 41 is located at one end of the programmer 40, and a button 42 that initiates the transmission is located at the other end. Three rotatable wheels 43-45 are provided to select or adjust the mode, time increment and direction. To set the timer device to 24 hours, as shown in FIG. 5, one would set the first mode wheel 43 to the setting for the countdown mode. Then the time increment would be set to hours using the second wheel 44. The third wheel 45 would then be turned until the LCD screen 46 read 24:00. Of course, this is only one way the programmer 40 could function. Buttons instead of rotatable wheels could be used, for example, similar to a TV remote control.

Figure 6:
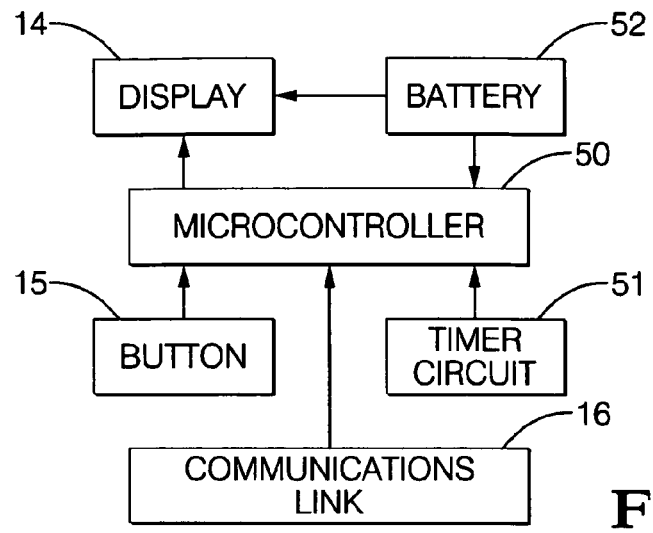
FIG. 6, is a block diagram showing the electrical components of the multifunction timer device.

The various electronic components contained on or connected to the printed circuit board 12 of the timer device 10, 20 will be explained with reference to FIG. 6. A programmable microcontroller 50 is provided on the printed circuit board 12 and arranged to receive timing information from a timer circuit 51. The microcontroller 50 outputs display signals to the display 14 for displaying timing information received from the timer circuit 51. A battery 52 is connected to the display 14 and to the microcontroller 50 for powering the device 10, 20. The microcontroller 50 receives operating and programming instructions from the multifunction input button 15 and from the external programmer 40 through the communications link 16.

The multifunction input button 15 is provided beside the display 14 in a convenient and intuitive location for operation by the user. The input button 15 is operable in a plurality of predetermined sequences to change the operating and display modes of the microcontroller 50 and/or the timer circuit 51. The predetermined sequences involve one or more presses of the input button 15 within a predetermined period of time. For example, a single press of the input button 15 will initiate a first control routine, two presses of the input button 15 within a short time period will initiate a second control routine, and three presses of the input button 15 within a short time period will initiate a third control routine.

A number of different circuit configurations can be used to produce a functioning timer device 10, 20. In the preferred embodiment, the printed circuit board 12 contains an oscillator that provides a very fast timed signal. This signal is then divided to provide pulses of more useful duration (e.g., seconds, minutes, hours).

A timer device 10, 20 is typically designed as either a count-up timer or a countdown timer. A count-up timer operates like a stopwatch and counts upward indefinitely. A countdown timer counts backwards from a preset start time. In the present invention, the timer device 10, 20 includes both a count up mode and a count down mode, which can be selected using the multifunction input button 15 to suit a particular application. If the timer device 10, 20 is set for counting up, the user can use the timer device 10, 20 for determining how long it had been since the timer had been activated. This function will be useful in situations where the useful life of an item is unknown, and qualitative decisions can be based on this time information. For example, two frozen dinners could be checked and the older one used first. For another example, one could tell at a glance how long it has been since the last pill was taken from a pill container.

In some applications, the count-up mode is not suitable or not best suited to associate a particular time to a particular task. For example, the count-up mode of the timer device 10, 20 does not give the user any frame of reference with which to judge the time information. The fact that an item (e.g., milk) has been on the shelf for a certain time period may not be sufficient information if the user does not know how long the item can be expected to last. In this case, the user may need a timer device having a countdown setting. The multifunction input button 15 of the present invention can be used to select the countdown mode for the timer device 10, 20 to suit these types of applications. In the countdown mode, the timer device 10, 20 has a predetermined end point (i.e., time zero). This makes it extremely useful for use with perishable goods and maintenance activities that must be performed at specific intervals.

Figure 7:
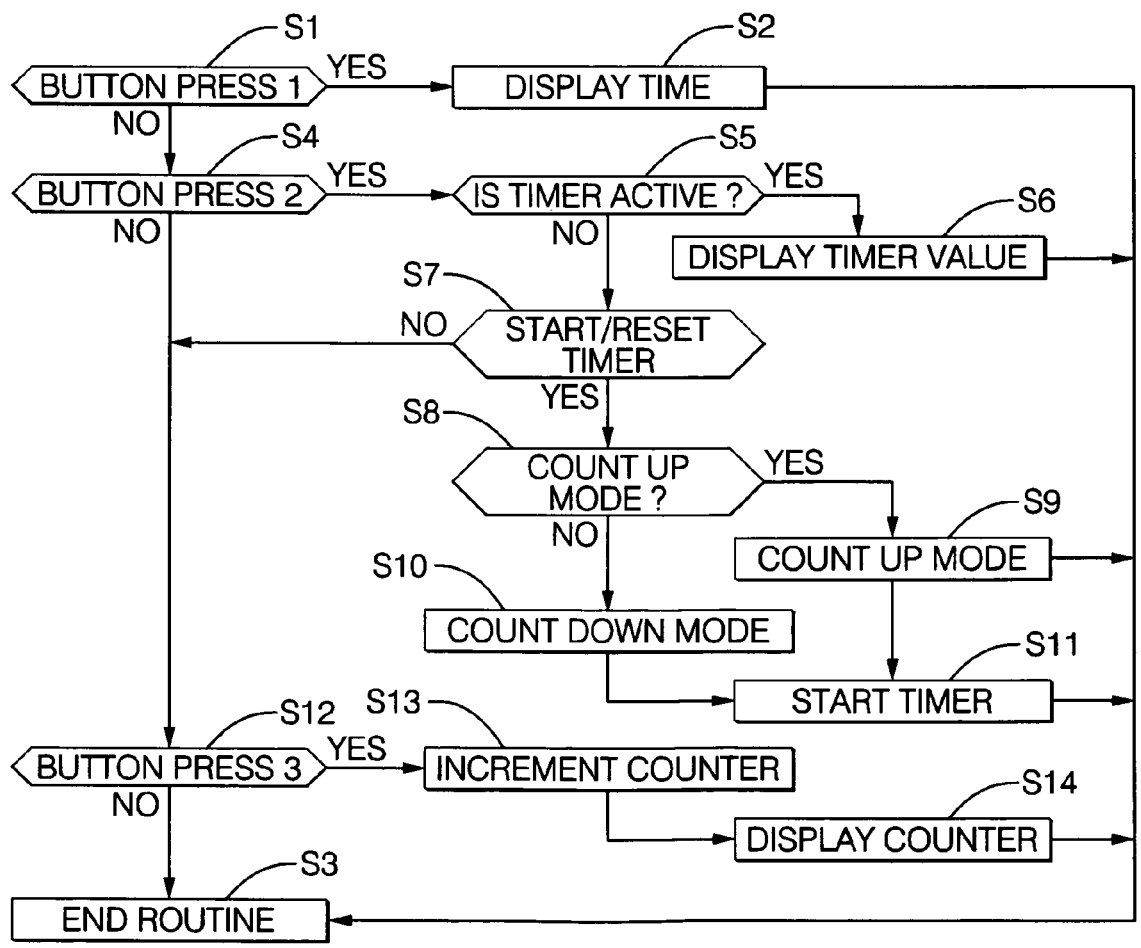
FIG. 7, is a flow chart showing the logic sequence used with the multifunction input button of the timer device.

FIG. 7 is a flow chart that illustrates some of the logic routines programmed into the microcontroller 50 in a preferred embodiment of the invention. The various logic routines are selectively activated by operating the multifunction input button 15 according to predetermined sequences, as explained above. A single press of the input button 15 is indicated at step S1 and causes the microcontroller 50 to awake from its power-conserving or "sleep" mode and to display a time/date on the display for a predetermined time period (e.g., 10 seconds) in step S2. The displayed time may be an actual or "real" time or a previously stored actual time, or an elapsed time since the button 15 was last pressed. It is understood that the type of time value displayed may be predetermined by the original programming of the microcontroller 50 or be determined by predetermined mode sequences. The control routine is then completed and passes to the end routine step S3 where the microcontroller 50 goes back into its sleep mode.

A double press of the input button 15 within a predetermined time period (e.g., 2 seconds) causes the control routine to go to step S4 and initiate a series of queries. The first query is to determine whether the timer is currently active, as indicated in step S5. That is, the microcontroller 50 will determine if the timer device 10, 20 is currently running in a timer mode. If the timer is currently active, the control routine will go to step S6 and display the timer value for a predetermined time period (e.g., 10 seconds). The control routine is then completed and passes to the end routine step S3 where the microcontroller 50 goes back into its sleep mode.

If the control routine determines in step S5 that the timer device 10, 20 is not currently active, the control routine will go to step S7 and display a message asking the user if he or she wants to start or reset the timer. If the user presses the input button 15 to indicate YES, the control routine will go to step S8. In step S8, the microcontroller 50 will display a message asking the user if he or she wants to set the timer circuit 51 in either a count-up mode, in which case the control routine goes to step S9, or a count-down mode, in which case the control routine goes to step S10. After the control routine sets the timer circuit 51 in the count-up mode or the count-down mode, the control routine goes to step S11 and the timer is started. The control routine is then completed and passes to the end routine step S3. If the user does not press the input button 15 for a predetermined time period (e.g., 10 seconds) in step S7, for example, the microcontroller 50 interprets this as a negative response and the control routine goes to step S12 or directly to the end routine step S3.

A triple press of the input button 15 within a predetermined time period (e.g., 3 seconds) causes the control routine to go to steps S12 and S13 to increment a counter contained on the printed circuit board 12. The counter information is then displayed on the display 14 in step S14. The control routine is then completed and passes to the end routine step S3 where the microcontroller 50 goes back into its sleep mode. This latter operating mode is useful for monitoring the taking of prescription pills by incrementing the counter when each pill is taken.

Docking Station

It is contemplated that the above-described timer device can be advantageously applied in pharmaceutical applications to enhance compliance by a patient in taking prescribed medications in accordance with a doctor's or pharmacist's instructions. The present invention provides an extremely inexpensive solution to provide cost effective connectivity between the patient and his medical-provider or professional. This arrangement has the related advantage of also facilitating record keeping by the medical provider or professional as well as affording the ability to provide both medically necessitated and commercial promotional messages to the customer/patient.

Although presently described in the context of a traditional pharmacy setting, it is contemplated that the docking station and method described herein, can be used with equal success in a hospital, dispensary, doctor's office or clinic, as well as in the patient's home. Furthermore, the present invention can be used for other applications, particularly items or material stored in a dispensing container having a short shelf-life, such biological materials or chemicals, or require precise record keeping (such as scientific research, law enforcement evidence retention, and the like).

Figure 8:
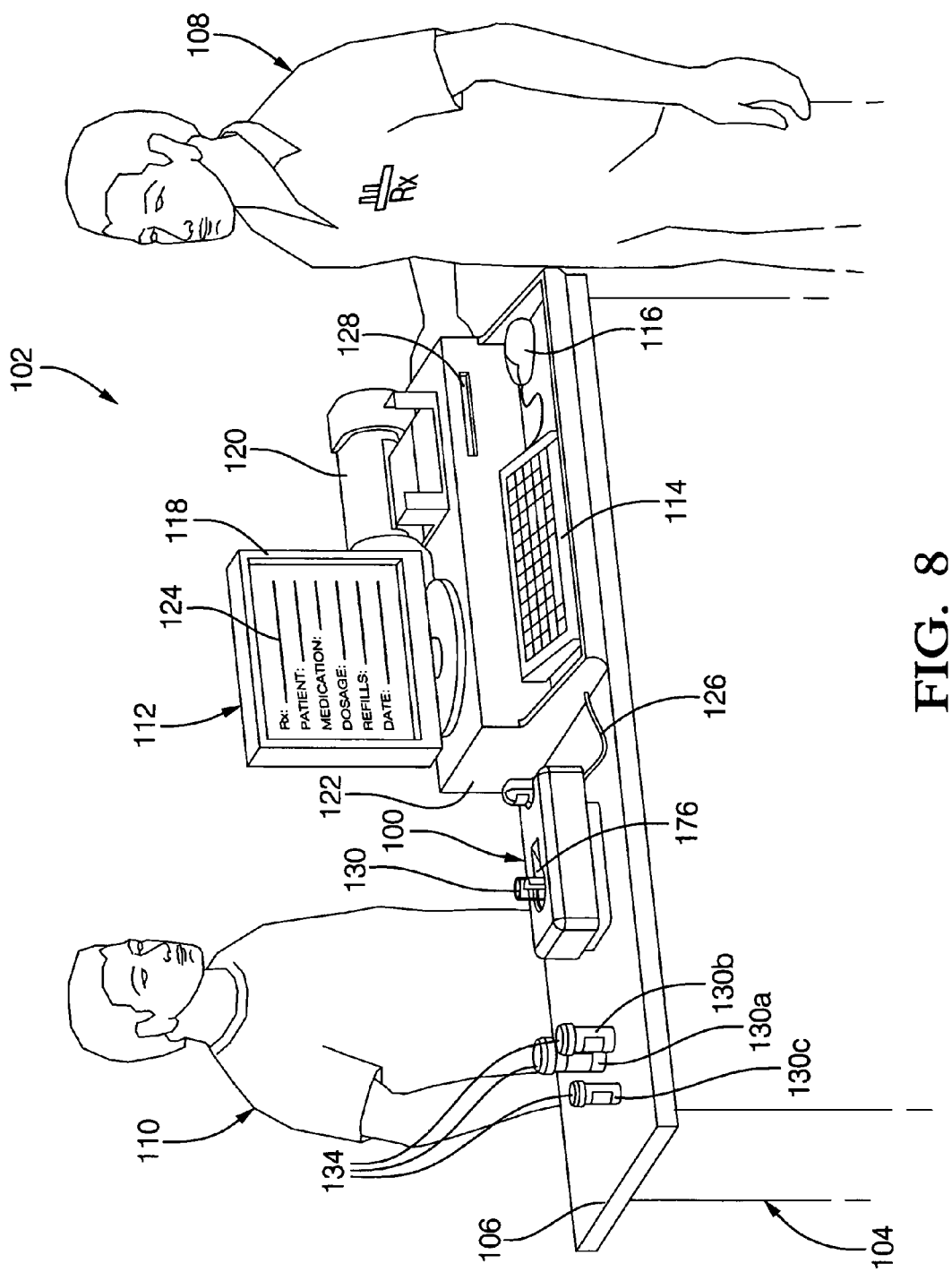
FIG. 8, is a perspective view of a preferred embodiment of the present invention employing a docking/programming station in a pharmaceutical point-of-sale application.

Referring to FIG. 8, a inexpensive docking station 100 is preferably employed at a point-of-sale location 102 such as a pharmacy counter 104 of the type equipped with an open, horizontal surface 106 located between a pharmacist 108 and a customer 110 for facilitating purchases of prescribed pharmaceuticals and associated goods, as well as related financial transactions and record keeping.

Transactions at the point-of-sale location 102 are typically facilitated by a record keeping system 112 including data entry devices, such as a keyboard 114 and mouse 116, a data display device or monitor 118 and a printer 120, all interconnected to a central computer 122 including a CPU and memory devices (not illustrated). The computer 122 is programmed to receive, record, process and store patient and prescription related data entered by the pharmacist 108 as well as to selectively display specific data 124 on the monitor 118. Preferably, the docking station 100 is located on the counter surface 106 for viewing and access by both the pharmacist 108 and the customer 110, and is interconnected with the record keeping system 112 via a cable 126, hard wiring, optical link, or other suitable interconnection means. In addition to data entered directly by the pharmacist 108, it is contemplated that data can also be derived from remote sources, portable devices, the internet, and the like. Accordingly, the meets and bounds of the record keeping system 112 is to be broadly defined.

The configuration illustrated in FIG. 8 is preferred because the docking station 100 can be easily interconnected with an existing host record keeping system 112 by the cable 126 using industry standard connectors and I/O ports (not illustrated). The docking station 100 can be provided as a "plug-and-play" device, containing pre-programmed memory. Additionally, the host record keeping system can be reprogrammed via a separate memory device (not illustrated), such as a compact disc configured for insertion in a disc drive 128 or other system I/O device.

As will be described in greater detail herein below, upon receiving a doctor's prescription or other legal authorization, the pharmacist 108 will enter all necessary data relevant for a given transaction into the system 112, wherein the newly entered data is stored and comingled with other related historical data concerning the customer 110. The current transaction data 124 is typically simultaneously displayed on the monitor.

Separately, the pharmacist 108 fills a container 130 with a prescribed quantity of medication, prints related patient data 124 on an adhesive label 132, applies the label 132 to an outer surface of the container 130, and presents the completed prescription (medication, container and label) to the customer 110 for confirmation and payment. The data 124 can be formatted in both alpha-numeric form to facilitate reading thereof and, separately, in a bar code for purposes of subsequent scanning for confirmation and prescription re-filling purposes.

At this point of the transaction, the customer 110 can be offered the option of electing to purchase a multifunction timer device 134, which will be attached to an associated container 130 and programmed via the docking station 100 to enhance compliance by a patient in taking prescribed medications in accordance with a doctor's or pharmacist's instructions. Furthermore, the multifunction timer device 134, once applied to the dispensing container and programmed, provides a cost effective connectivity between the patient and his medical-provider or professional. This arrangement has the related advantage of also facilitating record keeping by the medical provider or professional as well as affording the ability to provide both medically necessitated and commercial promotional messages to the customer/patient.

The basic operation of a preferred embodiment of the multifunction timer device 134 is described herein above in connection with FIGS. 1-7, and is the subject of the claimed inventions of U.S. Pat. No. 7,236,428 B1 and U.S. Ser. No. 11/803,272 filed 14 May 2007, which are owned by the common inventor/applicant.

Figure 20:
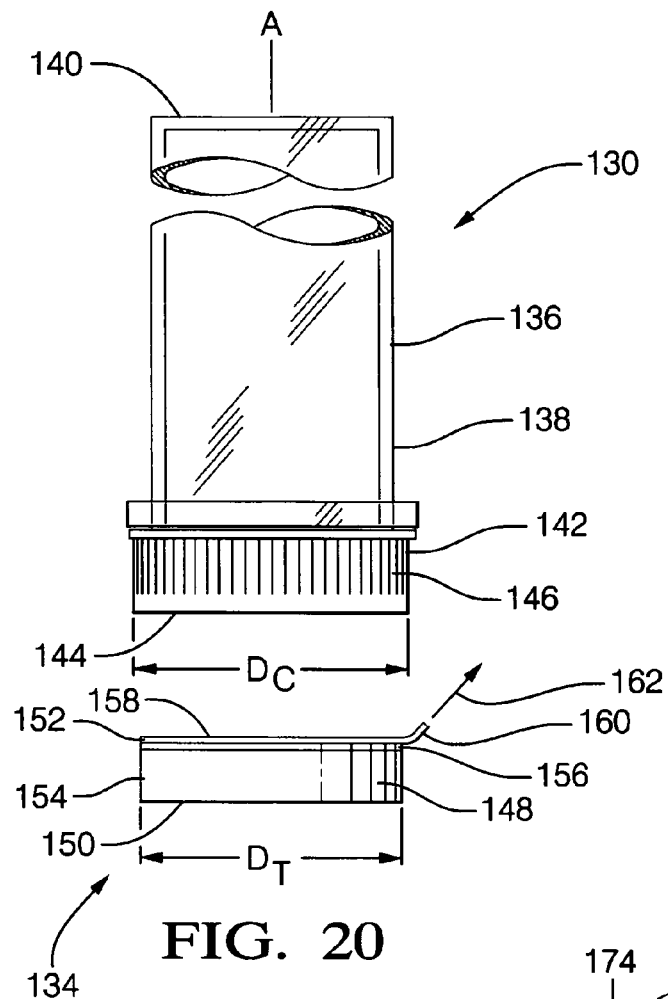
FIG. 20, is a broken, exploded plan view of an inverted dispensing container with the end surface of the container closure member juxtaposed with an exposed surface of a multifunction timer device configured for self-engagement via an intermediate layer of selectively exposable contact adhesive.
Figure 21:
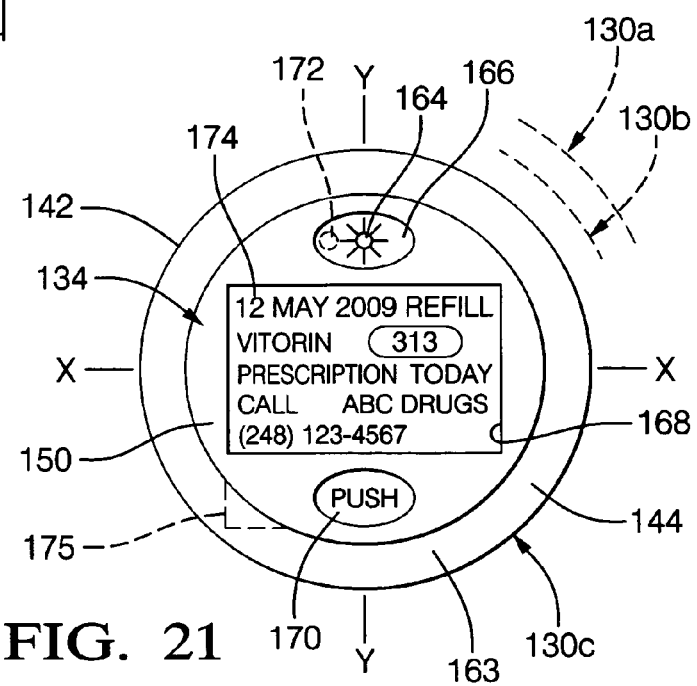
FIG. 21, is a bottom plan view of the multifunction timer device adhesively attached to the closure cap of the dispensing container of FIG. 20.

Referring to FIGS. 20 and 21, a dispensing container 130 for pharmaceutical applications typically comprises an open ended cylindrical vial 136 formed of injection molded, relatively rigid translucent plastic material. The vial 136 has an axially elongated cylindrical body portion 138 closed at one end by an end wall portion 140 and open at an opposed end. The open end of the vial 136 is selectively closed by a twist-off closure cap 142 formed of injection molded, moderately resilient opaque plastic material. The closure cap 142 has an end wall 144 and an axially extending axial skirt portion 146. When assembled, the cap 142 is secured to the open end of the vial 136 by retention means (not illustrated) such as a radially outwardly extending peripheral upset bead formed in the vial 136 adjacent the open end thereof, and a cooperating annular groove formed on the inner wall of the skirt portion 146. The cap 142 can be removed from the vial 136 simply by axially locally deforming the skirt portion 146 of the closure cap 142 to release the upset bead from its associated groove. It is contemplated that threaded screw-on type closure caps as well as so called "child-proof" closure caps can also be applied in the present invention.

Although depicted in an elongate, rectangular form in connection with the embodiments described in connection with FIGS. 1-7, the preferred configuration of the multifunction timer device 134 of the present invention is shown in FIGS. 20 and 21 and has a disc-shaped housing 148 defined by an upper or display side 150 (illustrated on the bottom in FIG. 20), an opposed lower or attachment side 152 (illustrated on the top in FIG. 20), and a peripheral sidewall 154. A layer of double-sided contact adhesive tape 156 is permanently adhered to the lower attachment side 152 of the closure cap 142. The exposed surface of adhesive tape 156 is temporarily covered by a removable protective cover 158, which is removed before attaching the multifunction timer device 134 to the end wall portion 144 of the closure cap 142. The protective cover 158 forms an outwardly extending pull tab 160 which facilitates its removal, as indicated by arrow 162.

As will be described in greater herein below, the multifunction timer device 134 is applied concentrically on the end wall portion 144 of the closure cap 142 or, alternatively, to the end wall portion 140 of the vial 136. The housing 148 of the multifunction timer device 134 has a nominal diameter designated Dt. The closure cap 142 has a nominal diameter designated Dc. Preferably, Dc is greater than Dt to define a step 163 on the end wall portion 144 of the closure cap 142.

The display side 150 of the multifunction timer device 134 includes three display/communication devices, an infrared light emitting diode (LED) 164 overlayed by a translucent diffuser 166, a liquid crystal display (LCD) 168 and a single push-button 170. Alternatively, a multi-color LED indicator light 172 (illustrated in phantom) also underlies the diffuser 166. The LED 164 provides a communication and programming link with the system 112 via the docking station 100. The LCD 168 functions to output alpha-numeric messages and information as well as pictograph displays (such as a picture of the pills contained in the container 130) to the customer 110. By way of example, the LCD can display information such as current date, time-of-day, urgent messages such as "take one pill before eating", call pharmacist for a refill", or "call doctor to renew prescription", the name and/or pictograph of the medication contained in the dispensing container, the name and telephone number of the drug store and similar information. Furthermore, the timer can be programmed by the patient to display only specifically defined information, can alternate between several fixed messages, or continuously stream information. The push-button 170 provides multifunction inputs to the timer device 134. The multi-color LED 172 indicator provides a number of color-coded timer status indications to the customer 110. With the exception of the descriptions which follow, the multifunction timer device 134 operates substantially similarly to the devices 10/20 of FIGS. 1-7.

Referring to FIG. 8, the Applicant has ascertained that, although available in a wide-ranging number of sizes and configurations, the vast majority of dispensing containers sold by large drug store chains are in one of three closure cap sizes (outside diameters)—1 3/16" (30 mm), 1 7/16" (36.5 mm) and 1 7/8" (47.6 mm). Accordingly, the preferred embodiment of the present invention is described with a focus on the most common container sizes. However, it is contemplated that the embodiments can be modified to accommodate other dispensing container sizes and configurations without departing from the spirit of the present invention.

FIG. 8 depicts the purchase of three differently sized dispensing containers 130a (large), 130b (medium) and 130c (small), each employing a similar multifunction timer device 134. A fourth dispensing container 130 is illustrated in an inverted position within a well 176 in the docking station 100. FIG. 21 illustrates the concentric juxtaposition of the multifunction timer device 134 with a small container 130c, as well as (in phantom) a medium container 130b and a large container 130a, along an axis of elongation designated A-A' extending normally out of and into the sheet bearing FIG. 21.

Referring to FIGS. 9-13, the details of a first alternative embodiment of a docking station 178 is illustrated. The docking station 178 consists of a generally box-shaped base portion 180, a platform portion 182, a bottom closure member 184 and a substrate or printed circuit board 186 upon which is mounted an infrared LED 188.

The base portion 180 consists of a one-piece structure injection molded of thermal plastic or similar material including a horizontally disposed top wall 190 with four side walls 192 extending downwardly there from in skirt-like fashion. An elongated rectangular depression 194 defined by four sides 196 and a bottom 198 extends downwardly from the top wall 190 a dimension which is slightly less than that of the side walls 192. A hollow generally cylindrical pedestal 200 extends upwardly from bottom 198 of depression 194 and is partially closed by a top surface 202. One or more openings 204 are formed in the top surface 202. A plurality of crescent-shaped upwardly directed pedestal extensions 206 are circumferentially arranged on the top surface 202 to form opposed cooperating guide surfaces 208. The top surface 202 and guide surfaces 208 of the pedestal 200 collectively define a pocket 210 configured for receiving and precisely positioning a top loaded multifunction timer device 212.

Figure 10:
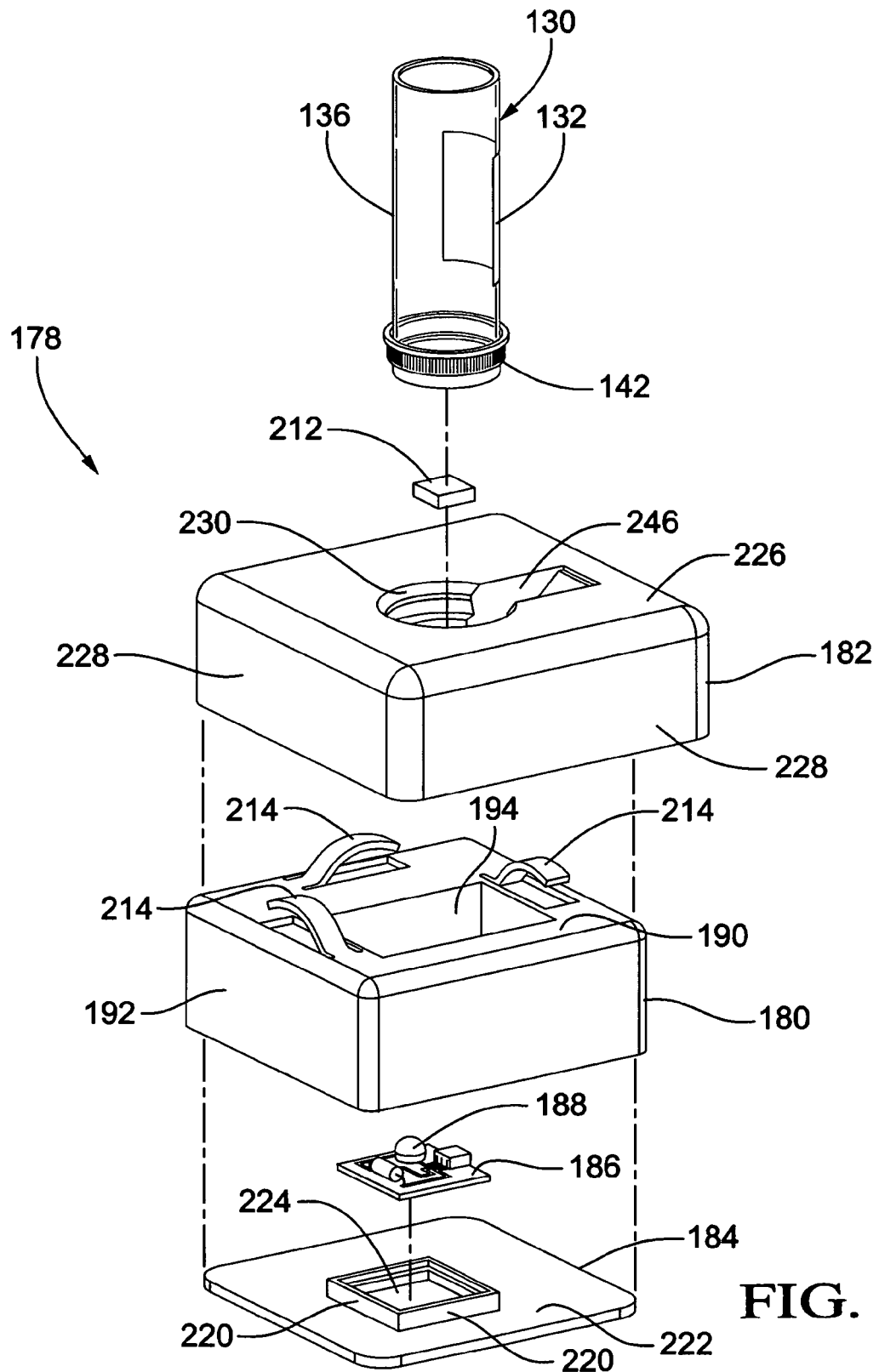
FIG. 10, is a perspective, exploded view of the first alternative embodiment of the docking station of FIG. 9 illustrating details of internal features thereof.
Figure 11:
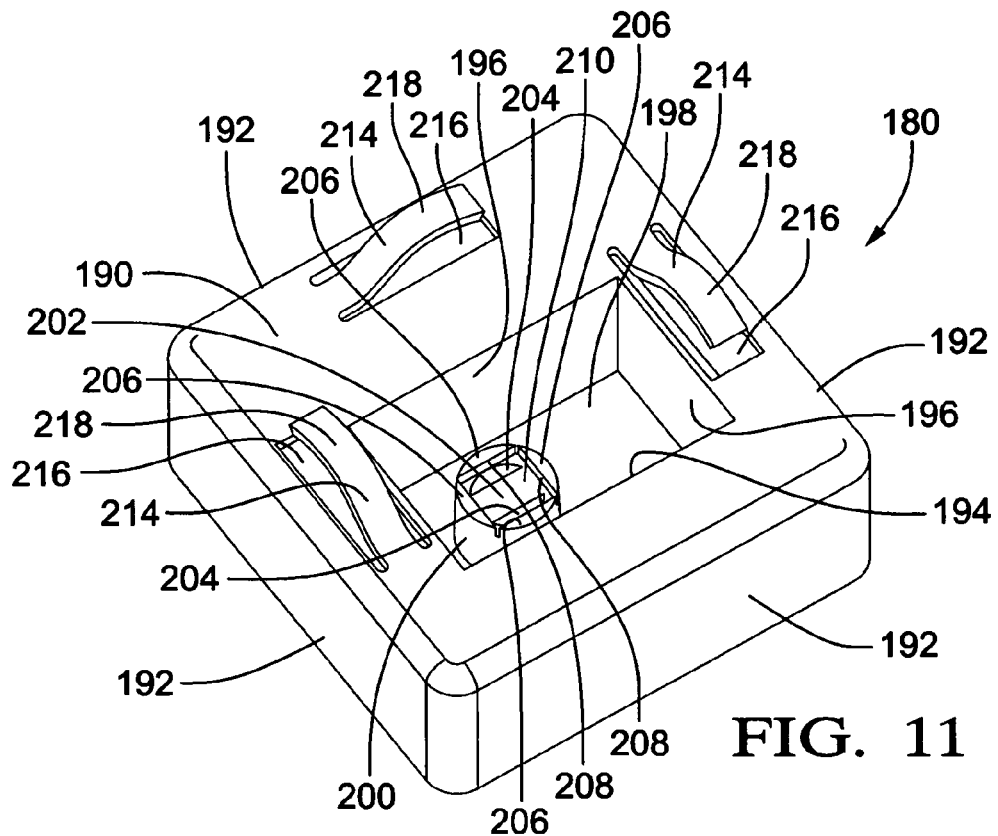
FIG. 11, is a perspective view of the base portion of the first alternative embodiment of the docking station of FIG. 9.
Figure 12:
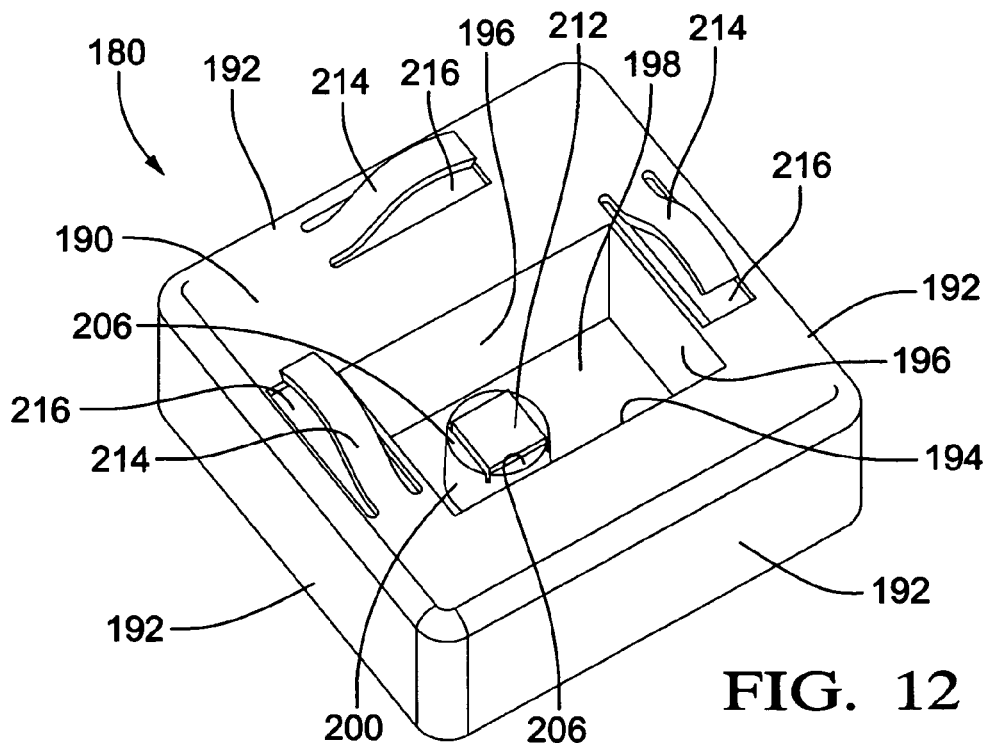
FIG. 12, is a perspective view of the base portion of the first alternative embodiment of the docking station of FIG. 9 with a multifunction timer device pre-positioned therein.

Each of a plurality (3 being depicted) of elongated cantilevered spring members 214 extend from corresponding openings 216 formed in the top wall 190 of the base portion 180. Each of the spring members 214 are curvalinearly formed along their respective lines of elongation to extend above the adjacent top wall 190 and define a contact or bearing surface 218 on the uppermost surface thereof. Preferably, three or more spring members are provided in an array which is circumferentially distributed about the periphery of the top wall 190. Thus, the resulting three contact surfaces 218 provide a stable supportive base for the platform portion 182 of the docking station 178. FIGS. 10-12 illustrate the spring members 214 in a relaxed condition, wherein no downward force in being applied, wherein the contact surfaces 218 are at their maximum elevation above the top wall 190.

Figure 9:
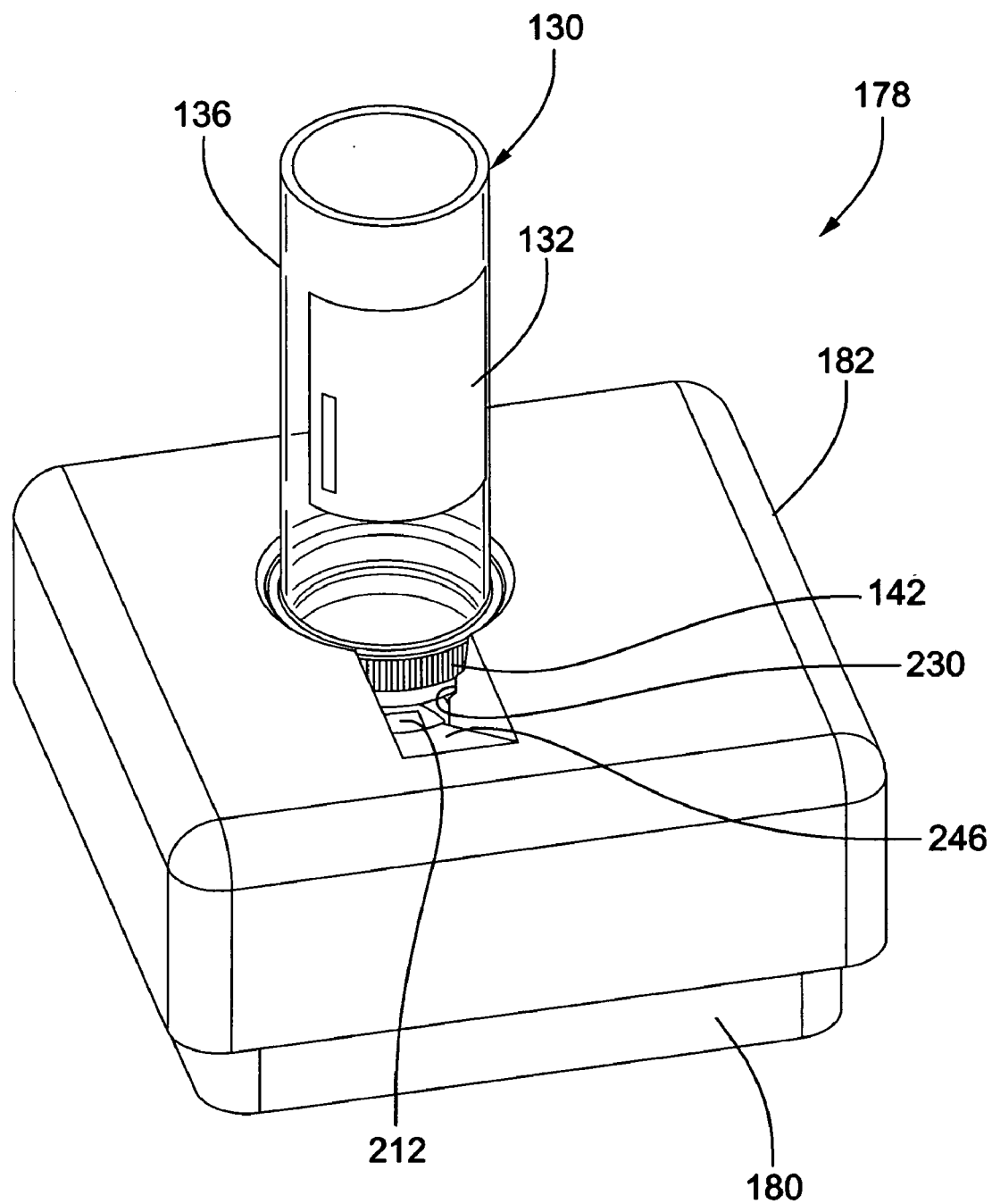
FIG. 9, is a perspective view of a first alternative embodiment of the docking station of FIG. 8 on an enlarged scale.

The spring members 214 are each integrally formed with the base portion 180 and have a natural resiliency provided by the base material employed. When downwardly directed force is applied upon the contact surfaces 218, the spring members 214 will be momentarily deflected downwardly until the contact surfaces 218 fall on the same plane as the remainder of the top wall 190. The application of further force will have no further effect. Upon release of the applied downward force, the natural resiliency of the spring members 214 will cause them to their illustrated configurations, thereby lifting the overlaying platform portion 182 to its extended or release position as illustrated in FIG. 9. Alternatively, the integral spring members 214 can be replaced with other resilient means such as discrete coil or leaf springs which simultaneously resiliently bear upwardly against the platform portion 182 and downwardly against the base portion 180.

Referring to FIG. 10, the bottom closure member 184 is provided to sealingly close the otherwise open bottom of base portion 180 and is affixed thereto by suitable attachment means such as fasteners (screws), adhesives, ultrasonic welding, hot staking, interference fit snap-engagement, or the like. The bottom closure member 184 is preferably formed if suitable injection molded thermoplastic material and is configured to cooperatively engage the lowermost portions of the base portion side walls 192. Upstanding guide walls 220 are integrally formed with the closure member 184 to extend above the upper surface 222 thereof and form an upwardly opening pocket 224 therewith. The pocket 224 is configured and dimensioned to nestingly fixedly receive the printed circuit board 186 therein. The infrared LED 188 extends above the printed circuit board 186 and is operative, when energized, to illuminate principally upwardly there from.

When assembled within the base portion 180, the LED 188 extends upwardly within the pedestal 200 and is positioned in substantial alignment with the pedestal openings 204 whereby infrared light emitted there from passes there through, flooding the pocket 210 to fully illuminate (in the IR spectrum) the exposed underside of the multifunction timer device 212 disposed therein.

As depicted in the embodiment of FIGS. 9-13, the multifunction timer device 212 is substantially square in outline, having four edge surfaces which, upon installation, are parallel to corresponding pedestal extension guide surfaces 208 to rotationally fixedly register the multifunction timer device 212 within the base pedestal pocket 210. This ensures maintenance of proper alignment of the "write" infrared LED 188 in the base portion assembly with the "read" infrared LED in the multifunction timer device 212 through the intermediate pedestal openings 204. Preferably, the pocket 210 and openings 204 are configured to ensure maintenance of optical alignment between the two infrared LEDs in any of the four potential orientations of the multifunction timer device 212 within the pocket 210.

The substantially round housing 148 of the multifunction timer device 134 depicted in FIGS. 20 and 21 is more problematic in regards to maintenance of rotational orientation between the multifunction timer device 134 when disposed in the base pedestal pocket 210. One solution is the provision of a radially outwardly extending nib 175 illustrated in phantom in FIG. 21. The nib 175 would be integrally formed to extend from the peripheral sidewall 154 and can be dimensioned and positioned such that, in application, the nib 175 is nestingly received within one of the four corners of the base pedestal pocket 210, thereby assuring the juxtipositioning of the multifunction timer device infrared LED 164 with the docking station base infrared LED 188 through intermediate openings 204. A more elegant solution is to configure the light openings 204 such that they produce omni-directional connectivity between the docking station base infrared LED 188 and the multifunction timer device infrared LED 164 through intermediate openings 204, whereby the requirement of precise rotational positional orientation of the multifunction timer device 134 during programming is effectively eliminated.

Although not illustrated in the embodiment of the invention depicted in FIGS. 9-13, it is contemplated that the printed circuit board 186 would carry other electrical circuit components, including a power source, memory, processing means, and the like, and, furthermore, be adapted for interconnection and communication with a host record keeping system 112 by a cable 126, remote interface, hard wiring or the like. Refer FIG. 8. Alternatively, the power supply for the printed circuit board 186 and the circuitry carried thereon can be supplied by a battery contained within the docking station 178 or a separate power cord (not illustrated).

The platform portion 182 consists of a one-piece structure injection molded of thermal plastic or similar material including a horizontally disposed top wall 226 with four side walls 228 extending downwardly there from in skirt-like fashion. The platform portion 182 is configured and dimensioned to slidingly receive the base portion 180 therein from below. When assembled, the underside surface of the platform top wall 226 bears downwardly against the contact surfaces 218 of the base spring members 214. When no externally applied load is present, the platform portion 182 is axially displaced a maximum dimension above the base portion 180 (first end limit of travel), and when an externally applied load sufficient to fully deflect the spring members 214 is present, the platform portion 182 is axially displaced a minimum dimension above the base portion 180 (second end limit of travel).

Although not illustrated, it is contemplated that retention means (clips, fasteners, or the like) can be provided to effectively interconnect the platform portion 182 with the spring members 214 to prevent inadvertent separation of the base portion 180 from the platform portion 182. Furthermore, the spring members 214 can, alternatively, be integrally formed with the platform portion 182 and extend to bear against the base portion 180, or both.

Figure 13:
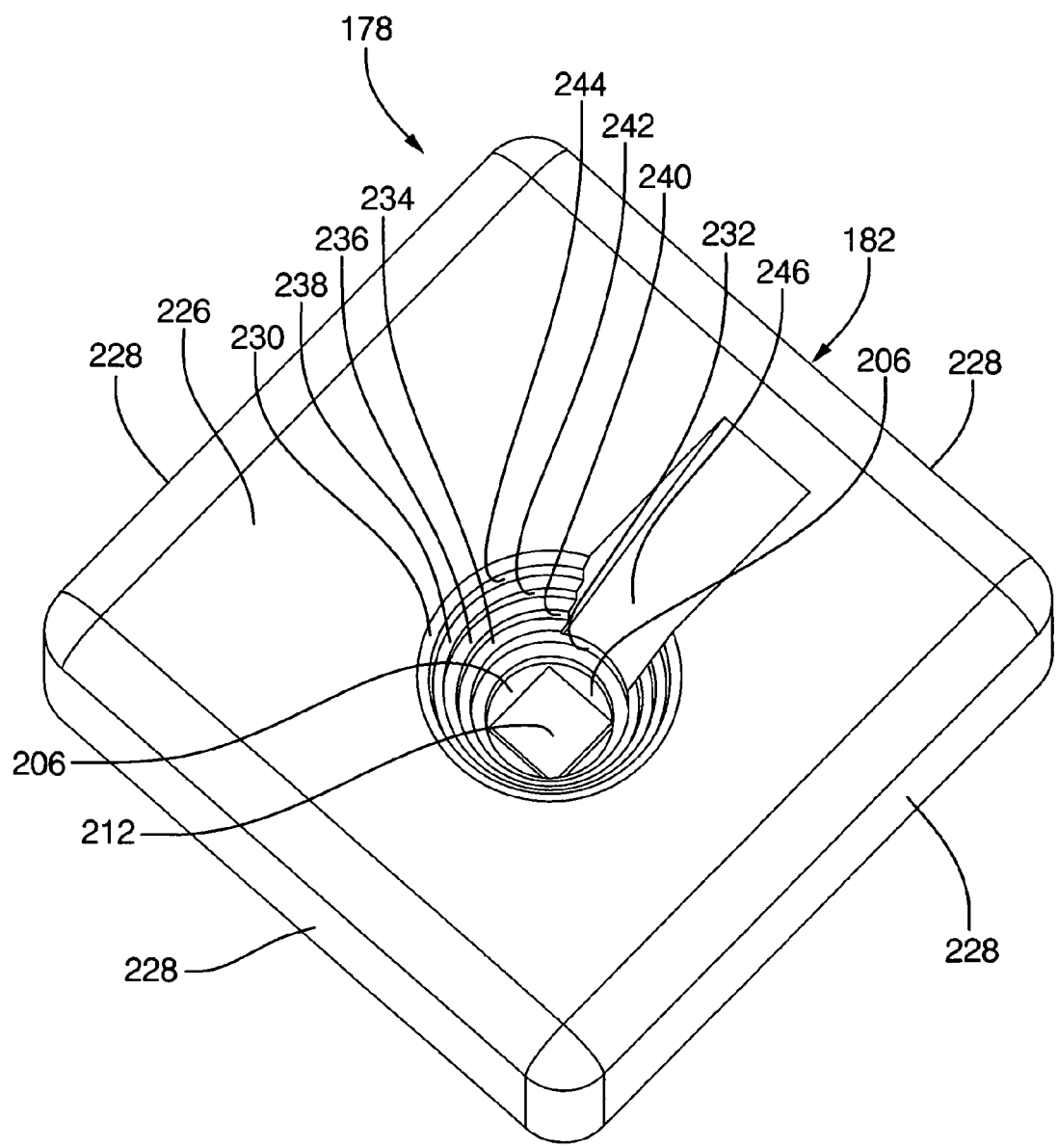
FIG. 13, is a perspective view of the platform portion of the first alternative embodiment of the docking station of FIG. 9 with the platform portion overlaying the base portion of FIGS. 11 and 12 and defining a well exposing portions of the base portion and the pre-positioned multifunction timer device.

As best illustrated in FIG. 13, a generally cylindrical recess or well 230 is integrally formed with and extends downwardly from the top wall 226 of the platform portion 182. The well 230 has a generally round bottom opening 232 which is slightly larger in diameter than that of the adjacent base pedestal 200, and is concentrically aligned therewith. Thus configured, multifunction timer devices 212 can be manually positioned within the pocket 210 of the base portion 180 by manual or mechanical insertion downward through the well 230.

The well 230 is tapered radially outwardly as it extends axially upwardly from the bottom opening 232 towards the top wall 226, and defines three discrete concentric radial steps 234, 236 and 238 having progressively increasing nominal diameters and spaced by axially extending risers or wall segments 240 and 242. Radial step 234 and adjacent riser 240 is configured and dimensioned to nestingly receive the closure cap 142c of the small standard container 130c in precise concentric alignment with a multifunction timer device 212 disposed in the base portion pocket 210. Step 234 also defines an axial downward limit of travel of the end wall portion 144c of the small diameter closure cap 142c.

Similarly, radial step 236 and adjacent riser 242 is configured and dimensioned to nestingly receive the closure cap 142b of the medium standard container 130b in precise concentric alignment with a multifunction timer device 212 disposed in the base portion pocket 210. Step 236 also defines an axial downward limit of travel of the end wall portion 144b of the medium diameter closure cap 142b. Furthermore, radial step 238 and an adjacent riser 244 is configured and dimensioned to nestingly receive the closure cap 142a of the large standard container 130a in precise concentric alignment with a multifunction timer device 212 disposed in the base portion pocket 210. Step 238 also defines an axial downward limit of travel of the end wall portion 144b of the large diameter closure cap 142a.

The platform portion 182 of docking station 178 has a sufficient amount of freedom of limited axial displacement between the first and second end limits of travel with respect to the base portion to enable engagement of the multifunction timer device 212 and the dispensing container 130 independent of which standard size is disposed within the well 230.

Thus configured, the well 230 of the present embodiment allows rapid repeated insertion of the end wall portion 144 of the closure cap 142 (refer FIGS. 20 and 21) of a dispensing container 130 of the three standard sized vials 136 without reconfiguring the docking station 178 or associated record keeping system 112. The present invention can be modified to accommodate more or fewer than three "standard" dimension dispensing containers 130. Furthermore, although it is preferred to mount the multifunction timer device 212 on the end wall portion 144 of the closure cap 142 of the dispensing container 130, if the well 230 were properly configured and dimensioned, the multifunction timer device 212 can alternatively be mounted on the end wall portion 140 of the vial 136 without departing from the spirit of the present invention.

A tapered trench 246 is integrally formed within the top wall 226 of the platform portion 182 of the docking station 178 extending radially outwardly continuously from the bottom opening 232 to the uppermost outer surface of the platform portion top wall 226. The trench 246 provides a clear line-of-sight for both scanning labels 132 in situ located anywhere on the outer peripheral surface of the vial 136 while deposited within the well 230. In application, this permits both visual confirmation of the presence and positioning of data displayed or carried on the label 132 as well as the ability to electronically scan the entire outer peripheral surface of the dispensing container 130.

Referring to FIGS. 12 and 13, the depression 194 formed in the base portion 180 is laterally elongated, with the pedestal 200 positioned off-center to the left providing a clearance region for the overlaying trench 246 formed in the platform portion 182. Thus, the trench 246 is disposed within the clearance region of the depression 194 and spaced from its adjacent sides 196 and bottom 198 throughout displacement of the platform portion 182 between the first and second end limits of travel.

It is contemplated that the first alternative embodiment of the invention illustrated in FIGS. 9-13 would employ a handheld scanner unit (not illustrated) which would be part of the record keeping system 112. Thus, in application, the pharmacist 108 would manually position the scanner parallel with the line of elongation of the trench 246 while rotating the dispensing container 130 about its axis A-A' to illuminate the entire outer peripheral surface of the dispensing container 130 including the label 132 and any supplemental instruction notices contained thereon.

Figure 14:
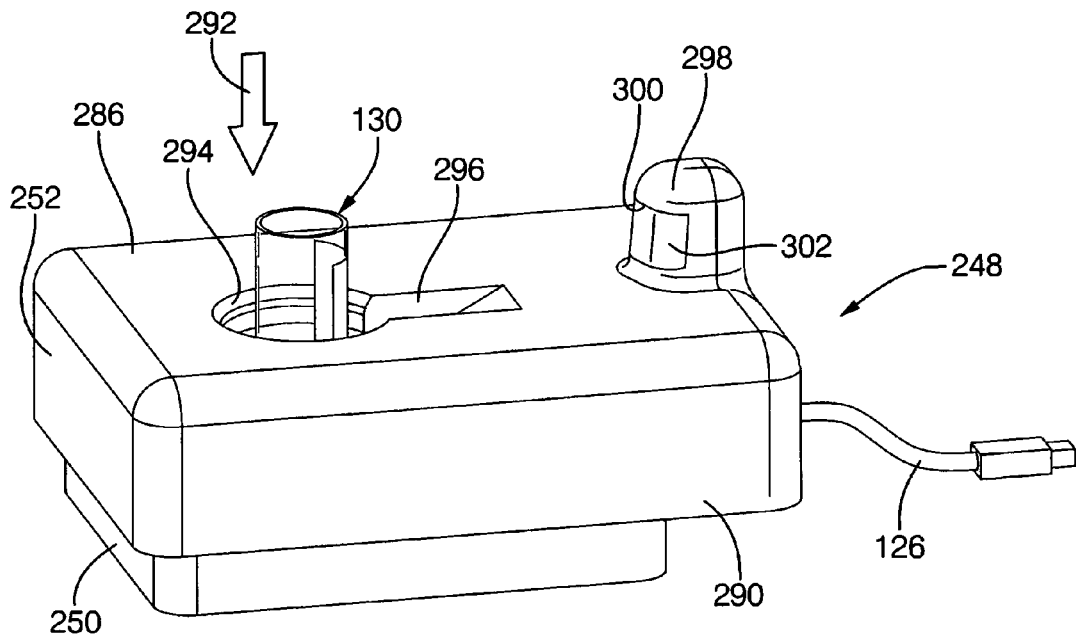
FIG. 14, is an upper perspective view of the embodiment of the docking station illustrated in FIG. 8 on an enlarged scale.
Figure 15:
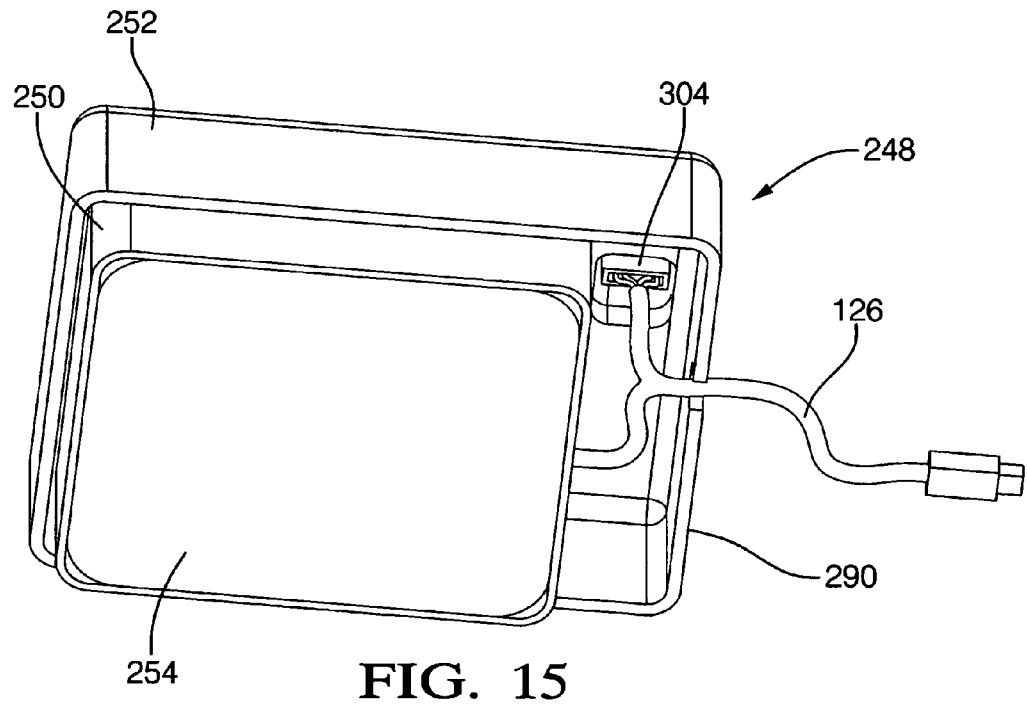
FIG. 15, is a lower perspective view of the embodiment of the docking station illustrated in FIG. 8 on an enlarged scale.
Figure 16:
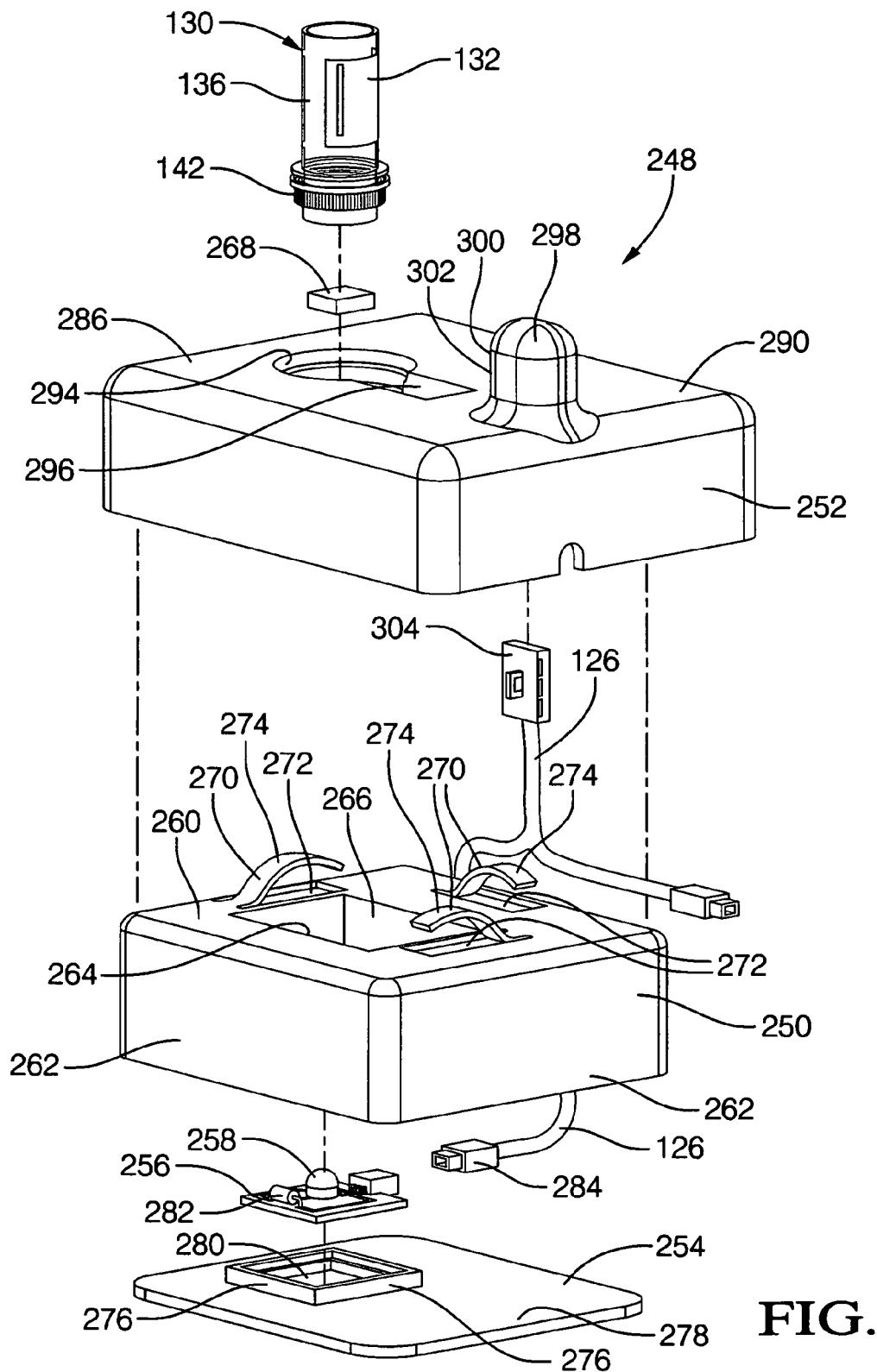
FIG. 16, is a perspective, exploded view of the embodiment of the docking station of FIGS. 14 and 15 illustrating details of internal features thereof.

Referring to FIGS. 14-16, the details of the preferred embodiment of a docking station 248 are illustrated. The preferred embodiment of the invention is illustrated in application with the record keeping system 112 in FIG. 8. The docking station 248 consists of a generally box-shaped base portion 250, a platform portion 252, a bottom closure member 254 and a substrate or printed circuit board 256 upon which is mounted an infrared LED 258.

The base portion 250 is substantially similar to the above described base portion 180, and consists of a one-piece structure injection molded of thermal plastic or similar material including a horizontally disposed top wall 260 with four side walls 262 extending downwardly there from in skirt-like fashion. An elongated rectangular depression 264 defined by four sides 266 and a bottom extends downwardly from the top wall 260 a dimension which is slightly less than that of the side walls 262. A hollow generally cylindrical pedestal extends upwardly from bottom of depression 264 and is partially closed by a top surface. One or more openings are formed in the top surface. A plurality of crescent-shaped upwardly directed pedestal extensions are circumferentially arranged on the top surface to form opposed cooperating guide surfaces. The top surface and guide surfaces of the pedestal collectively define a pocket configured for receiving and precisely positioning a top loaded multifunction timer device 268.

Each of a plurality (3 being depicted) of elongated cantilevered spring members 270 extend from corresponding openings 272 formed in the top wall 260 of the base portion 250. Each of the spring members 270 are curvalinearly formed along their respective lines of elongation to extend above the adjacent top wall 260 and define a contact or bearing surface 274 on the uppermost surface thereof. Preferably, three or more spring members are provided in an array which is circumferentially distributed about the periphery of the top wall 260. Thus, the resulting three contact surfaces 274 provide a stable supportive base for the platform portion 252 of the docking station 248. FIG. 16 illustrates the spring members 270 in a relaxed condition, wherein no downward force in being applied, wherein the contact surfaces 274 are at their maximum elevation above the top wall 260.

The spring members 270 are each integrally formed with the base portion 250 and have a natural resiliency provided by the base material employed. When downwardly directed force is applied upon the contact surfaces 274, the spring members 270 will be momentarily deflected downwardly until the contact surfaces 274 fall on the same plane as the remainder of the top wall 260. The application of further force will have no further effect. Upon release of the applied downward force, the natural resiliency of the spring members 270 will cause them to their illustrated configurations, thereby lifting the overlaying platform portion 252 to its extended or release position as illustrated in FIG. 14. Alternatively, the integral spring members 270 can be replaced with other resilient means such as discrete coil or leaf springs which simultaneously resiliently bear upwardly against the platform portion 252 and downwardly against the base portion 250.

Referring to FIGS. 15 and 16, the bottom closure member 254 is provided to sealingly close the otherwise open bottom of base portion 250 and is affixed thereto by suitable attachment means such as fasteners (screws), adhesives, ultrasonic welding, hot staking, interference fit snap-engagement, or the like. The bottom closure member 254 is preferably formed of suitable injection molded thermoplastic material and is configured to cooperatively engage the lowermost portions of the base portion side walls 262. Upstanding guide walls 276 are integrally formed with the closure member 254 to extend above the upper surface 278 thereof and form an upwardly opening pocket 280 therewith. The pocket 280 is configured and dimensioned to nestingly fixedly receive the printed circuit board 256 therein. The infrared LED 258 extends above the printed circuit board 256 and is operative, when energized, to illuminate (in the IR spectrum) principally upwardly there from.

When assembled within the base portion 250, the LED 258 extends upwardly within the pedestal and is positioned in substantial alignment with the pedestal openings whereby infrared light emitted there from passes there through, flooding the pocket formed by the pedestal to fully illuminate (in the IR spectrum) the exposed underside of the multifunction timer device 268 disposed therein.

In the preferred embodiment of the docking station 248 depicted in FIGS. 8 and 14-16, the printed circuit board 256 carries other electrical circuit components 282, including a controller, a memory, processing means, and the like, which are interconnected by circuit traces. Furthermore, the printed circuit board 256 communicates directly with the host record keeping system 112 by cable 126 interfaces by a connector 284.

The platform portion 252 consists of a one-piece structure injection molded of thermal plastic or similar material including a horizontally disposed top wall 286 with four side walls 288 extending downwardly there from in skirt-like fashion. The platform portion 252 is configured and dimensioned to slidingly receive the base portion 250 therein from below and is elongated longitudinally in one dimension to define an overhang 290 extending externally of an adjacent side wall 288. When assembled, the underside surface of the platform top wall 286 bears downwardly against the contact surfaces 274 of the base spring members 270. When no externally applied load is present, the platform portion 252 is axially displaced a maximum dimension above the base portion 250 (first end limit of travel), and when an externally applied load, designated by an arrow 292 in FIG. 14, sufficient to fully deflect the spring members 270 is present, the platform portion 252 is axially displaced a minimum dimension above the base portion 250 (second end limit of travel).

As best illustrated in FIGS. 14 and 16, a generally cylindrical recess or well 294 is integrally formed with and extends downwardly from the top wall 286 of the platform portion 182. The well 294 has a generally round bottom opening, which is slightly larger in diameter than that of the adjacent base pedestal, and is concentrically aligned therewith. Thus configured, multifunction timer devices 268 can be manually positioned within the pocket of the base portion 250 by manual or mechanical insertion downward through the well 294.

The well 294 is tapered radially outwardly as it extends axially upwardly from the bottom opening towards the top wall 286, and defines three discrete concentric radial steps having progressively increasing nominal diameters and spaced by axially extending risers or wall segments which are configured and function substantially as depicted in FIG. 13.

A tapered trench 296 is integrally formed within the top wall 286 of the platform portion 252 of the docking station 248 extending radially outwardly continuously from the bottom opening to the uppermost outer surface of the platform portion top wall 286. The trench 246 extends longitudinally along centerline of the platform portion 252 and provides a clear line-of-sight for both scanning labels 132 in situ located anywhere on the outer peripheral surface of the vial 136 while deposited within the well 294. In application, this permits both visual confirmation of the presence and positioning of data displayed or carried on the label 132 as well as the ability to electronically scan the entire outer peripheral surface of the dispensing container 130.

Referring to FIG. 16, the depression 264 formed in the base portion 250 is longitudinally elongated, with the pedestal positioned off-center to the left providing a clearance region for the overlaying trench 296 formed in the platform portion 252. Thus, the trench 296 is disposed within the clearance region of the depression 264 and spaced from its adjacent sides 266 and bottom throughout displacement of the platform portion 252 between the first and second end limits of travel.

A upwardly extending, generally dome-shaped turret 298 is integrally formed on the centerline of the top wall 286 of the platform portion 252 of the docking station 248 in the overhang 290 portion thereof. A window 300 formed in the turret 298 is aligned with and faces the tapered trench 296 such that a direct line-of-sight between the turret window 300 and the exposed portion of a dispensing container 130 disposed within the well 294 is maintained. The window 300 is closed by a transparent or translucent lens 302 which defines the field of view.

A scanner 304 is mounted within the turret 298 disposed with a field of view extending through the window 300 and centered upon the tapered trench 296. The scanner is interconnected with the record keeping system 112 via the cable 126. Preferably, the scanner 304 is a bar code imager such as those produced by Microscan as "MS" series Auto ID Barcode Readers. Such devices are typically of compact construction to facilitate embedding in a host device, provide high speed reading, have a relatively wide range-of-view, can provide symbol reconstruction and can be readily customizable with the software of the host system.

The scanner 304 is mounted for movement with the platform portion 252 and, thus, with the target dispensing container 130 disposed within the well 294. This ensures maintenance of precise alignment between the two, and thus, accuracy of the scanning process, even while the target dispensing container 130 is being rotated within the well, and while the multifunction timer device 268 is being affixed to the dispensing container 130.

Figure 18:
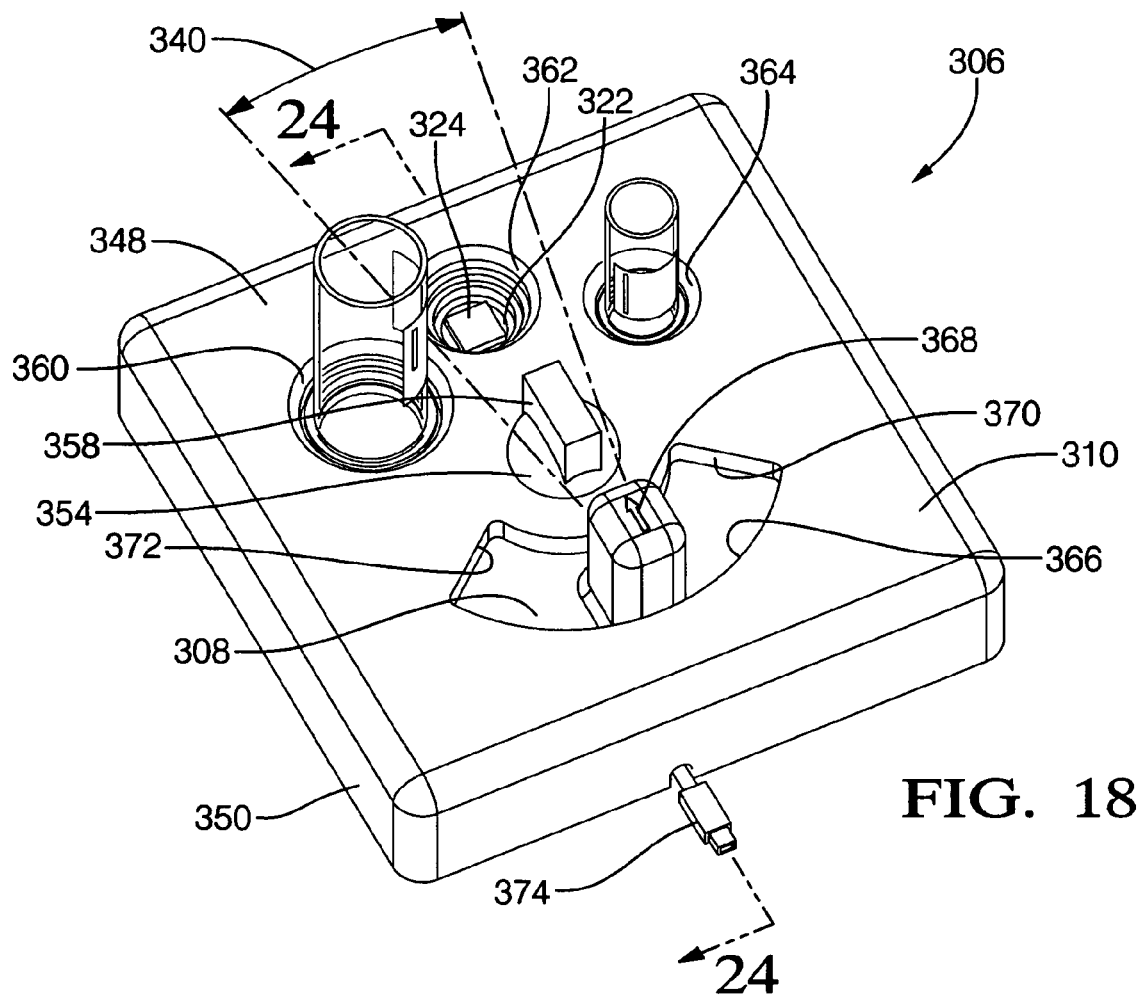
FIG. 18, is an upper perspective view of a second alternative embodiment of the docking station of FIG. 8 on an enlarged scale.
Figure 19:
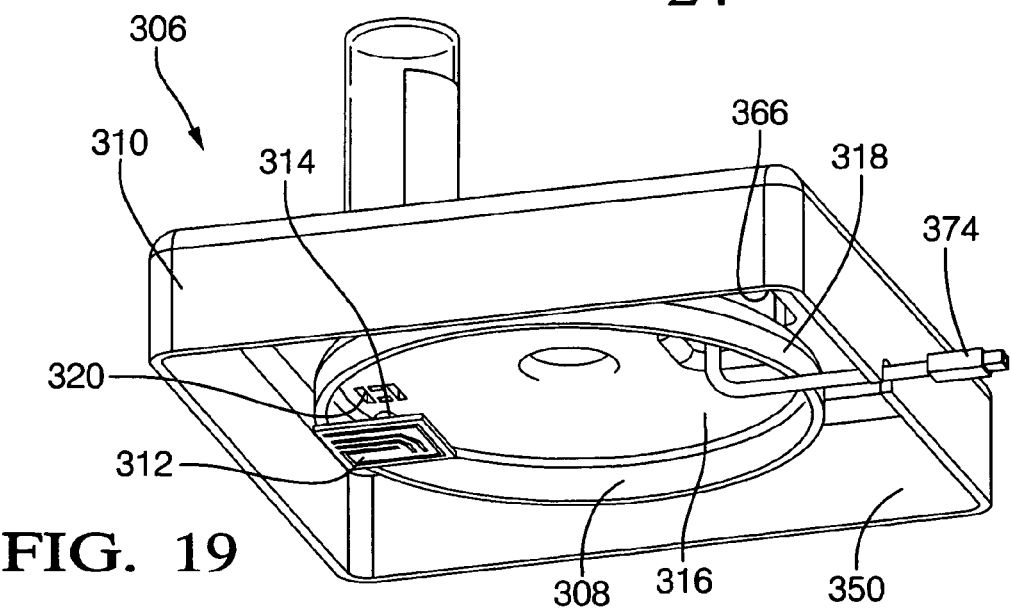
FIG. 19, is a lower perspective view of the second alternative embodiment of the docking station illustrated in FIG. 18 with the bottom closure member removed to expose internal details.
Figure 24:
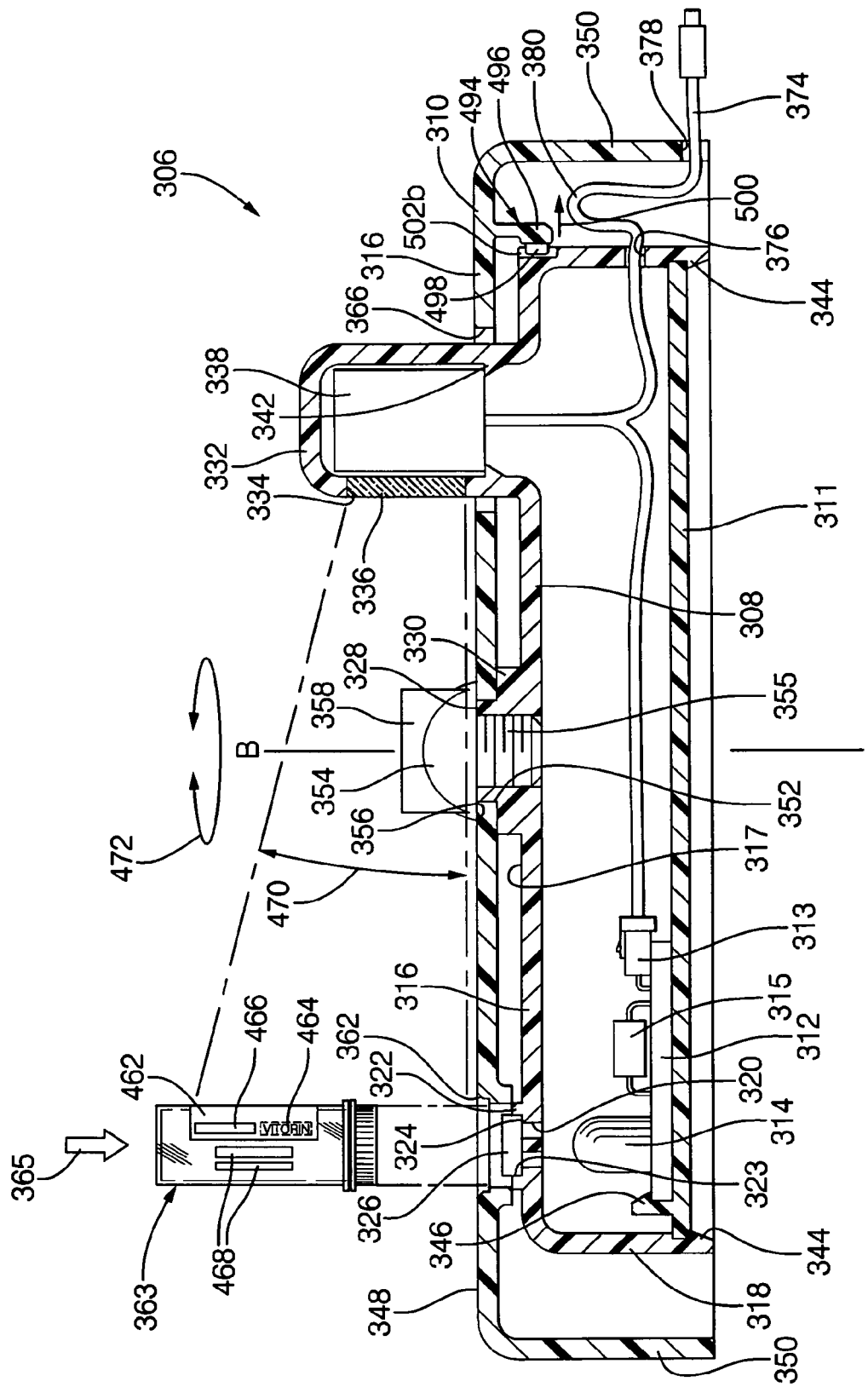
FIG. 24, is a cross-sectional view, taken on lines 24-24 of FIG. 18.

Referring to FIGS. 18, 19 and 24, the details of a second alternative embodiment of a docking station 306 is illustrated. The docking station 306 consists of a generally cylindrically-shaped base portion 308, a platform portion 310, a bottom closure member 311 and a substrate or printed circuit board 312 upon which is mounted an infrared LED 314, other electrical components such as an integrated controller circuit package 315, a connector 313, and interconnecting conductive traces (not illustrated).

The base portion 308 consists of a one-piece structure injection molded of thermal plastic or similar material including a horizontally disposed circular top wall 316 with a cylindrical side wall 318 extending downwardly there from in skirt-like fashion. One or more openings 320 are formed in the top wall 316 in alignment with the LED 314. A plurality of crescent-shaped upwardly directed extensions 322 are circumferentially arranged on the upper surface 317 of the top wall 316 to form opposed cooperating guide surfaces 323. The upper surface 317 of top wall 316 and guide surfaces 323 of the extensions 322 collectively define a pocket 324 configured for nestingly receiving and precisely positioning a top loaded multifunction timer device 326. The openings 320 and extensions 322 are formed near the outer edge of the top wall 316 adjacent the side wall 318.

The base portion 308 includes an integral tubular hub 328 and a concentric bushing 330 extending above the top wall 316 and defining an axis of rotation B-B'. The base portion 308 further includes an integral vertically elongated turret 332 extending above the top wall 316 near the outer edge thereof adjacent the side wall 318 and opposed 180° about the axis B-B' from the extensions 322. The turret 332 is hollow and has a window 334 in a wall thereof facing the opposed extensions 322. The window 334 is closed by a lens 336. A scanner or bar code reader 338 is nestingly disposed in the upper end of the turret 332 and is positioned to direct its field of view radially toward the multifunction timer device 326 and extensions 322 as illustrated by an arrow 340 in FIG. 18. The scanner 338 is retained in the turret 332 by snap-fit tabs 342 or the like. Preferably, the scanner is positioned to read the label of a single dispensing container at a time.

The bottom closure member 311 is affixed to the inner diameter surface of the sidewall 318 by snap-fit tabs 344 or the like. Furthermore, the printed circuit board 312 is mounted in its illustrated position on the upper surface of the bottom closure member 311 by integral snap-fit tabs 346, guide walls, or the like.

The platform portion 310 consists of a one-piece structure injection molded of thermal plastic or similar material including a horizontally disposed top wall 348 with four side walls 350 extending downwardly there from in skirt-like fashion. The platform portion 310 is configured and dimensioned to receive the base portion 308 therein from below. When assembled, the bottom edge surfaces of the base portion side walls 318 and the bottom edge surfaces of the platform portion side walls 350 simultaneously rest upon the horizontal counter surface 106. Refer FIG. 8.

The platform portion 310 has a central axial opening 352 in the top wall 348 thereof. When assembled, the underside surface of the platform portion top wall 248 bears downwardly against the base portion bushing 330. The base hub 328 extends upwardly through the platform portion central opening 352 to form a pivot joint there between, wherein the base portion 308 and platform portion 310 are vertically restrained but are otherwise free to rotate about axis B-B' with respect to one another. A threaded lock member 354 includes a central shaft 355 which engages the threaded inner diameter surface of the hub 328. A radially outwardly directed head of the lock member 354 defines a bearing surface 356 which, when tightened, bears downwardly against the upper surface of the platform portion top wall 348. Definitionally, the lock member 354 constitutes locking means which selectively, releasably interconnects the platform portion and the base portion to prevent relative rotational displacement there between about axis B-B'. The exposed uppermost portion of lock member 354 extending above the platform portion 310 defines flats 358 configured to facilitate manual loosening (to allow limited relative freedom of rotation between the base portion 308 and the platform portion 310) and tightening (to interlock the base portion 308 with the platform portion 310).

As best illustrated in FIG. 18, the top wall 348 of the platform portion 310 forms a first (large) generally cylindrical recess or well 360, a second (intermediate) generally cylindrical recess or well 362, and a third (small) generally cylindrical recess or well 362. The wells 360, 362 and 264 are each integrally formed with and extend downwardly from the top wall 348 of the platform portion 310. The wells 360, 362 and 264 each have a generally round bottom opening which is larger in diameter than that of the base portion extensions 322. As illustrated, the extensions 322 are collectively concentrically aligned with the intermediate sized well 362. Thus configured, multifunction timer devices 326 can be manually positioned within the pocket 324 of the base portion 308 by manual or mechanical insertion downward through one of the wells 360, 362 or 264. The three wells 360, 362 and 364 are circumferentially spaced and radially equidistant from the axis B-B' of rotation of the base portion 308 and platform portion 310 of the docking station 306.

Contrasted with the wells described herein above, the wells 360, 362 and 364 configured for a single size of dispensing container can be much shallower in axial depth. Accordingly, there may be no need for a trench to accomplish scanning of the entire outer peripheral surface of the dispensing container. An appropriately sized dispensing container 363/130, when inserted within well 362, as indicated by an arrow 365, nests therein in precise concentric alignment with the multifunction timer device 326 for immediate affixation therewith.

The turret 332 extends upwardly through a crescent-shaped opening 366 formed in the top wall 348 of the platform portion 310. The opening 366 provides the user convenient access to the base portion 308 and defines the first and second end limits of rotational travel there between. The outer surfaces of the turret 332 can be grasped and manipulated as a handle. Furthermore, the turret 332 is radially elongated to continuously "point" radially inwardly toward the single particular well 360, 362 or 364 with which it is registered. A radially inwardly directed arrow 368 reinforces this orientation.

Referring to FIG. 18, the base portion 308 is illustrated in its center of rotational freedom, wherein the arrow 368 on the turret 332 points towards the intermediate well 362, and the timer receiving pocket 324 is registered therewith. Should the user desire to reconfigure the docking station 306 to process a large or small dispensing container, he would begin by first loosening the lock member 354. Then, he would rotate the turret handle 332 either rightwardly to reposition the timer pocket 324 under the large well 360 (wherein the turret handle 332 abuts a righthandmost wall 370 of the crescent opening 366—one "end limit of travel"), or, alternatively, rotate the turret handle 332 leftwardly to reposition the timer pocket 324 under the small well 364 (wherein the turret handle 332 abuts a lefthandmost wall 372 of the crescent opening 366—another "end limit of travel"). This repositioning is indicated by an arrow 472. Thereafter, he would retighten the lock member 354 and proceed with the processing.

As in the case of the previously described embodiments of the invention, the printed circuit board 312 and the scanner 338 are interconnected with a host record keeping system 112 by a cable 374 dressed through openings 376 and 378 in the base portion side wall 318 and platform portion side 350, respectively. A slack portion 378 is provided in the cable 374 radially intermediate the respective side walls 318 and 350 to accommodate the limited relative rotation between the base portion 308 and platform portion 310 of the docking station 306.

The docking station 306 is distinguishable from the previously described embodiments wherein the uppermost surfaces of the base portion extensions 322 are in coplanar alignment with the exposed upper surface of a multifunction timer device 326 disposed in the pocket 324. The uppermost surfaces of the base portion extensions 322 collectively define a stop for a dispensing container being inserted within the operative well 360, 362 or 364. By contrast, in the above described embodiments, the well of each provides a step which defines a stop for a dispensing container.

Referring to FIG. 24, three haptic detents 494 are configured within the docking station 306, each operative to provide a tactile indicator of precise axial alignment of the guide pocket 324, as well as a multifunction device 326 disposed therein, with one of the three wells 360, 362 or 364. As indicated, by way of example, the intermediate well 362 and underlying guide pocket 324 (with multifunction timer device 326), are registered. The haptic detent 494 consists of an elongated tab 496 integrally formed with and extending downwardly from the lower surface of the top wall 348 of the platform portion 310. The tab 496 has a radially inwardly directed cam face 498 extending in interference fit with the radial outermost surface of the side wall 318 of the base portion 308 which, in all possible positions, other than the three aligned positions described herein above, will ride upon the base outer sidewall 318 and resiliently deflect the tab 496 radially outwardly as indicated by an arrow 500.

Three circumferentially spaced, single, downwardly extending notches 502a, 502b and 502c (with only notch 502b being illustrated), are formed on the outer surface of the base side wall 318 to selectively engage the tab cam face 498 therein. Each notch 502 is circumferentially aligned with a corresponding well 360, 362 and 364. As illustrated, the cam face 498 extends within the center notch 502b to precisely align the intermediate well 362 with the timer pocket 324, thereby providing the operator a tactile indication. The operator can override the detent action by manually urging the turret handle 332 in one direction or the other. When the detent 494 is engaged, the tab 496 is in a relaxed position (indicated) with the cam face 498 disposed within the notch 502b. Thereafter, the platform portion 310 is releasably engaged with the base portion 308 by the locking member 354.

As in the case of all other embodiments of the docking stations described herein, the scanner 338 has a field of view allowing it to scan the entire outer peripheral surface of the dispensing container 363 applied thereto as the container 363 is rotated about its axis of elongation within the well 362. The container 363 typically has a label 462 with fields containing pertinent alpha-numeric or pictograph data 464, as well as data in bar code format 466. Also, supplemental cautionary or informational labels 468 are frequently applied to the container 363. As best viewed in FIG. 18, the scanner 338 has a horizontal field of view defined by arrow 340. As best viewed in FIG. 24, the scanner 338 has a vertical field of view defined by an arrow 472.

Referring to FIG. 22, an alternative design dispensing container 380 for pharmaceutical applications typically comprises an open ended cylindrical vial 382 formed of injection molded, relatively rigid translucent plastic material. The vial 382 has an axially elongated cylindrical body portion 384 closed at one end by an end wall portion (similar to the end wall portion 140 of FIG. 20) and open at an opposed end. The open end of the vial 382 is selectively closed by a twist-off closure cap 386 formed of injection molded, moderately resilient opaque plastic material. The closure cap 386 has an end wall 388 and an axially extending axial skirt portion 390. When assembled, the cap 386 is secured to the open end of the vial 382 by retention means (not illustrated) such as a radially outwardly extending peripheral upset bead formed in the vial 382 adjacent the open end thereof, and a cooperating annular groove formed on the inner wall of the skirt portion 390. The cap 386 can be removed from the vial 382 simply by axially locally deforming the skirt portion 390 of the closure cap 386 to release the upset bead from its associated groove. It is contemplated that threaded screw-on type closure caps as well as so called "child-proof" closure caps can also be applied in the present invention.

Although depicted in an elongate, rectangular form in connection with the embodiments described in connection with FIGS. 1-7, an alternative preferred configuration of the multifunction timer device 392 of the present invention is shown in FIG. 22 and has a disc-shaped housing 394 defined by an upper or display side 396 (illustrated on the bottom in FIG. 22), an opposed lower or attachment side 398 (illustrated on the top in FIG. 22), and a peripheral sidewall 400. A plurality of circumferentially arranged engagement tabs 402 are integrally formed and extend axially upwardly from the attachment side 398 of the multifunction timer device housing 394.

The closure cap 386 has an annular extension 404 integrally formed therewith depending end wall 388. The extension 404 has a ramped head portion 406 interconnected to the end wall 388 by a reduced diameter neck portion 408. The transition point between the head portion 406 and neck portion 408 comprises a radially extending flat surface or catch 410.

The multifunction timer device 392 is attached to the closure cap 386 by axially compressing the two together, whereby the engagement tabs 402 are momentarily deflected radially outwardly by contact with the tapered head portion 406, followed by resilient snap-engagement of the tabs 402 with the catch surface 410 for positive retention.

Referring to FIG. 23, a reconfigurable well 412 for a docking station 414 is illustrated. Rather than being integrally formed with the platform portion, the well 412 can be removed and replaced with another well to accommodate dispensing containers of differing dimensions. The well 412 is formed separately from the platform portion 418 of the associated docking station 414. The top wall 416 of the platform portion 418 of the docking station 414 has a passageway 420 formed by a stepped boss 422. The stepped boss includes an axially extending threadform 424 therein. The well 412 preferably formed of injection molded plastic or other suitable material. The well 412 is formed as a cylindrical wall 426 with a reduced diameter opening 428 at the bottom end thereof formed by a radially inwardly directed step or flange. The upper surface 432 defines a stop for dispensing containers inserted within the well 412. The opening 428, in application is aligned with an infrared LED as described herein above.

The top end of the cylindrical wall 426 terminates in a thickened section or collar 434 which has an axial threadform 436 on the outer surface thereof configured to releasably engage the platform portion threadform 424. The collar 434 terminates in a radially outwardly extending flange 438 which, when the well 412 is fully installed, abuts the upper surface of the top wall 416 and ensure precise positioning thereof. The outer circumferential surface of the flange 438 has knurls or flats 440 to accommodate tools for installing/removing the well 412.

The well 412 is configured to axially receive a large size dispensing container having a maximum nominal diameter designated D1. A first cylindrical insert 442 (illustrated in phantom) is configured to be nestingly disposed within the well 412. The first insert 442 has a radially inwardly directed step 444 at the bottom portion thereof to define an upper surface or stop 446 for dispensing containers inserted within the first insert 442. The top end of the first insert 442 termi-nates in an outwardly directed flange 448 which, when the first insert 442 is fully installed, abuts the top of the well flange 438 to ensure precise positioning thereof. The first insert 442 is configured to axially receive an intermediate size dispensing container having a maximum nominal diameter designated D2. A second cylindrical insert 450 (illustrated in phantom) is configured to be nestingly disposed within the first insert 442. The second insert 450 has a radially inwardly directed step 452 at the bottom portion thereof to define an upper surface or stop 454 for dispensing containers inserted within the second insert 450. The top end of the second insert 450 terminates in an outwardly directed flange 456 which, when the second insert 450 is fully installed, abuts the top of the first insert flange 448 to ensure precise positioning thereof. The second insert 450 is configured to axially receive a small size dispensing container having a maximum nominal diameter designated D3.

It is contemplated that fewer or more inserts can be concentrically stacked to provide a differing degree of reconfigurability such as if more than three "standard" dispensing container sizes were employed at a retail outlet such as that depicted in FIG. 8. Furthermore, because differing sized replicable wells and inserts may be provided for use with a standardized docking station 414, decorative or instructional indicia 458 (illustrated in side view as raised lettering) can be applied on a visible (ex.: top surface) surface 460 of the flange 438 of the reconfigurable well 412. Typical indicia 458 could include the name of the service provider (ex.: "ABC DRUGS") or the size dispensing containers appropriate for the insert set (ex.: "USE WITH 30 MM, 36.5 MM AND 47.7 MM VIALS ONLY"). To further facilitate reconfiguration and use of properly sized wells and inserts, they can be coded in different contrasting colors.

Figure 17:
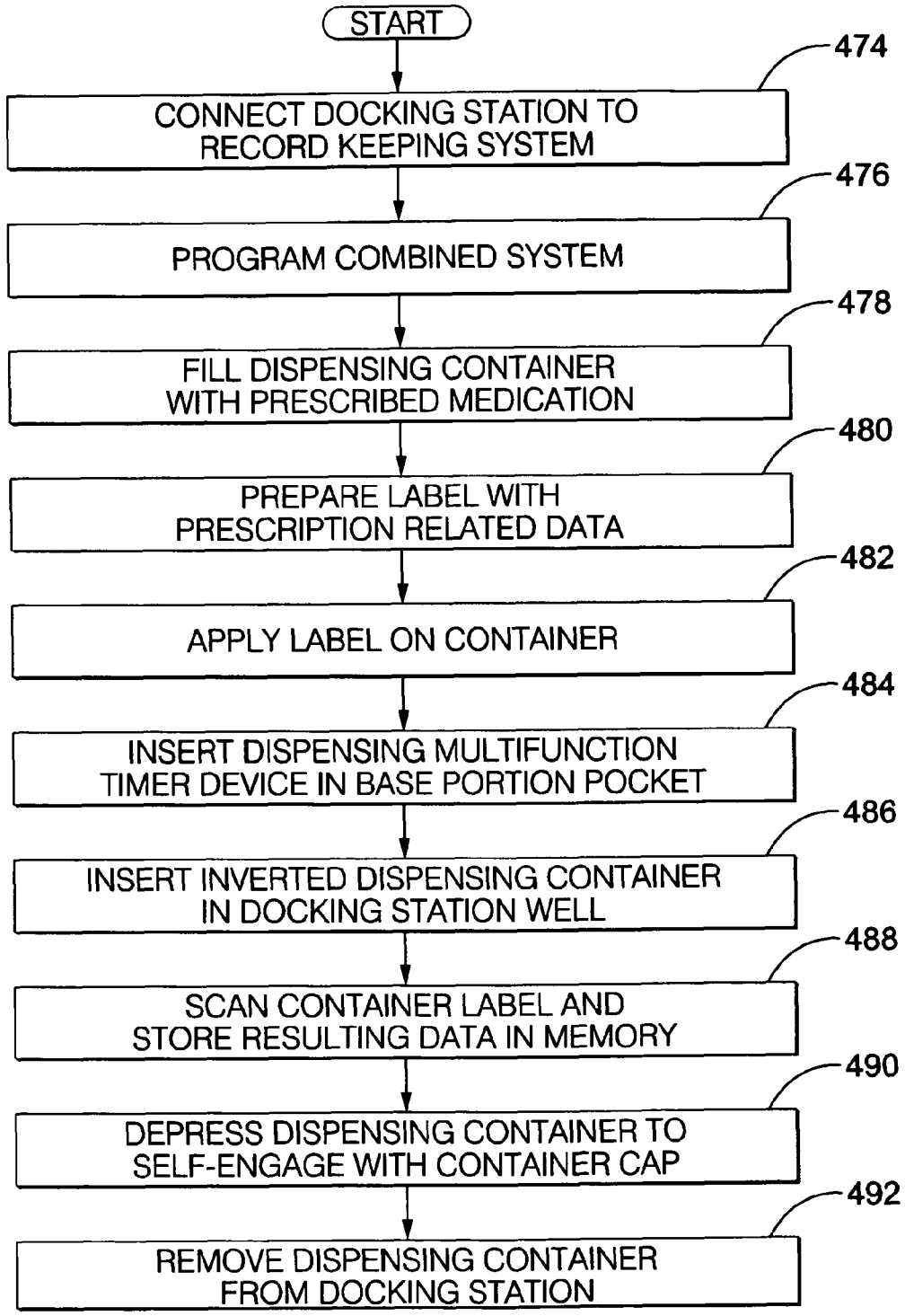
FIG. 17, is a flow chart showing the method of mounting and programming the multifunction timer device at the pharmaceutical point-of-sale illustrated in FIG. 8.

Referring to FIGS. 8 and 17, the methodology of employing the preferred embodiment docking station 100/248 is described. For purposes of descriptive clarity, the contemplated primary use of one of the docking stations 100, 178, 248 and 306 described herein, will focus on a point-of-sale setting 102 of a health care provider, such as a pharmacy. It is contemplated that the docking station 248 can also be employed in a non-retail setting such as a hospital dispensary, a doctor's office or clinic, or a private residence or office. Furthermore, any of the described embodiments can be employed successfully. The following description is intended as an example on only one of a number of possible scenarios.

Prior to any related transactions, the docking station 248 is interconnected to a standard port of an existing pharmacy record keeping system 112 via flexible cable 126 (step 474). The record keeping system 112 is disposed on sales counter 104 and is provided with keyboard 114 and mouse 116, data display device or monitor 118 and printer 120, all interconnected to central computer 122 including a CPU and memory devices (not illustrated). The computer 122 is programmed to record, process and store patient and prescription related data entered by the pharmacist 108 as well as to selectively display specific data 124 on the monitor 118. Preferably, the local portion of the docking station 248 is located on the counter surface 106 for viewing and access by both the pharmacist 108 and the customer 110, and is interconnected with the record keeping system 112 via the cable 126, hard wiring, optical link, or other suitable interconnection means. As stated herein above, the record keeping system 112 can have remote portions or interconnections with other devices. This arrangement can prove to promote marketing and sales of multifunction timer devices to the relevant (pharmacy) customer base.

Following connection of the docking station 248, the aggregate system is programmed via pre-existing plug-and-play coding in memory devices contained in the docking station controller and/or coding in separate machine-readable media, such as a pre-loaded compact disc sold with the docking station 248 (step 476).

In a typical transaction, a customer 110 will present a prescription document provided by his doctor to the pharmacist 108 for filling. Following standard protocol, the pharmacist 108 will enter all necessary information received from the customer 110 or on the prescription document into the system 112 via the keyboard 114, mouse 116, wand-type hand-held scanner (not illustrated), or similar I/O device.

After receiving any required authorizations and consulting the customer's history contained in the system memory, the pharmacist will "fill" the prescription by filling a vial 136 with the specified type and amount of medication and sealingly closing the vial 136 with a closure cap 142 (step 478). Thereafter, he will consult the data 124 displayed on the system monitor 118 to verify accuracy and then prepare an adhesive backed label 132 and any supplemental labels 468 (step 480) and then apply the label(s) to the outer peripheral surface of the container vial 136 (step 482). The displayed data typically includes: the drugs name, address and telephone number, a prescription number, the date filled, the original prescription date, the patient's name, address and telephone number, the (proprietary or generic) name, dosage, type (tablet, capsule, liquid, device, etc.) and number or amount of the medication within the container 130, instructions concerning patient's taking (consumption or applying) medication, the prescribing doctor's name, address and telephone number, the number of prospective refills currently available, the drug's efficacy expiration date, as well as any supplemental instructions concerning taking with or without food, operating dangerous equipment, other medications, possible side effects, and the like.

Upon confirming the accuracy of the newly entered data, it is written into and stored within the system memory. Simultaneously the scanner 304 is (or continues to be) activated.

Upon receiving the customer's approval to include a multifunction timer device 134 with a newly filled prescription, the pharmacist 108 will select a new multifunction timer device 134 from an inventory behind the counter 104 and install it within the docking station well 176 with its display side 150 facing downwardly and its attachment side 152 facing upwardly after removing any protective cover 158. Once having passed through the well 176, the multifunction timer device is rotationally manipulated by the pharmacist to nestingly fit into the docking station base pocket 210 to axially align the multifunction timer device 134 with the well 176 (step 484).

Next, the pharmacist 108 will preferably invert the dispensing container 130 whereby the end wall portion 144 of the closure cap 142 is directed downwardly. Once substantially aligned with the vertical axis of the well 176, the container is placed within the well 176 to assume concentric alignment with a correspondingly dimensioned riser wall segment 240, 242 or 244 and displaced downwardly until the leading end wall portion 144 abuts a corresponding step 234, 236 or 238, thereby limiting its downward axial displacement within the well 176 (step 486).

The dispensing container 130 is then manually rotated about its axis of elongation to expose the external circumferential surface thereof to the scanner 304, whereby the scanner 304 reads the container label 132 as well as any supplemental labels 468 and encodes the information contained therein and stores the encoded information in the host system processing system (step 488). When a scan is complete, such as when the controller/processor detects it has read redundant information within a short time period (ex. 1-2 seconds), indicating a full scan of the entire circumferential surface of the dispensing container 130 has taken place, an enunciator located in the docking station controller 315 or the host record keeping system 112 will issue an audible tone. Simultaneously, selected encoded data is written into the multifunction timer device 268 via the optical coupling between the infrared LED 258 writer in the docking station base 250 and the adjacent infrared LED reader 164 carried on the display side 150 of the multifunction timer device 134. In addition, the controller can query the host system database to access other data, such as the current date, time of day, and pictographs of the appearance of the medication in the dispensing container 130 and trademarks/logos of the drug store previously stored in the record keeping system 112 can be read into the multifunction timer device 134.

After scanning and programming of the multifunction timer device 134 is complete, the dispensing container 130 is manually depressed downwardly to establish intimate contact of the exposed attachment side surface of the multifunction timer device 134 with the end wall portion 144 of the closure cap 142 of the dispensing container 130. In so doing, the multifunction timer device 134 self-engages the closure cap 142 (step 490).

Lastly, the fully assembled dispensing container 130 and programmed multifunction timer device 134 is removed from the docking station 248 and presented to the customer 110 (step 492). For transactions involving multiple prescriptions, the above process is repeated. Although it is believed that the multifunction timer device 134 can be designed and produced sufficiently inexpensively to justify its being disposable after a single use, a previously programmed, functioning multifunction timer device 134 which is still affixed to its associated closure cap 142 can be reused by following the above described steps and "rewriting" new or updated data over previous data.

While the invention has been specifically described in connection with specific embodiments thereof, it is to be understood that this is by way of illustration and not of limitation, and the scope of the appended claims should be construed as broadly as the prior art will permit.

It is to be understood that the invention has been described with reference to specific embodiments and variations to provide the features and advantages previously described and that the embodiments are susceptible of modification as will be apparent to those skilled in the art.

Furthermore, it is contemplated that many alternative, common inexpensive materials can be employed to construct the basis constituent components. Accordingly, the forgoing is not to be construed in a limiting sense.

The invention has been described in an illustrative manner, and it is to be understood that the terminology, which has been used is intended to be in the nature of words of description rather than of limitation.

Obviously, many modifications and variations of the present invention are possible in light of the above teachings. For example, a fully functioning docking station apparatus could be built into a record keeping system. As a second example, the system can be configured whereby the infrared LEDs on the docking station base assemblies and the multifunction timer devices can effect two-way communication there between, whereby the multifunction timer device programming can be modified by the patient, who subsequently downloads the changes into the host record keeping system. It is, therefore, to be understood that within the scope of the appended claims, wherein reference numerals are merely for illustrative purposes and convenience and are not in any way limiting, the invention, which is defined by the following claims as interpreted according to the principles of patent law, including the Doctrine of Equivalents, may be practiced otherwise than is specifically described.

Having thus described the invention, what is claimed as new and desired to be secured by Letters Patent is as follows:

1. A docking station for programming and mounting a multifunction timer device to a dispensing container, said docking station comprising:
    a base portion operative to fixedly support an infrared light emitting diode (LED), said base portion including guide walls forming a pocket for receiving and pre-positioning a multifunction timer device in alignment with said LED for optical coupling there between;
    a platform portion carried on said base portion, said platform portion defining a well configured to nestingly retain a dispensing container therein in substantial axial alignment with said base portion pocket, said well including guide walls operative to concentrically align and axially position an end surface of a dispensing container disposed therein with an exposed surface of said prepositioned multifunction timer device;
    means to effect axial engagement between said container end surface and exposed timer surface;
    a scanner having a field of focus directed toward an outer peripheral surface of a dispensing container positioned within said well and operable for encoding information imprinted thereon; and
    a controller adapted for electrically interconnecting said LED and scanner with a host data processing system, said controller operative to write selected data to said multifunction timer device via said LED optical coupling as a function of said encoded information and related data stored in said host data processing system.

2. The docking station of claim 1, wherein said scanner is carried for displacement with said platform portion.

3. The docking station of claim 1, wherein said platform portion is disposed for limited relative axial displacement between first and second end limits of travel with respect to said base portion, whereby an end surface of a dispensing container is axially spaced from an exposed surface of a multifunction timer device in said first end limit of travel and in surface-to-surface contact in said second limit of travel.

4. The docking station of claim 3, further comprising resilient means operative to continuously urge said platform portion into said first position.

5. The docking station of claim 4, wherein said resilient means comprises a compression spring.

6. The docking station of claim 4, wherein said resilient means comprises at least one cantilever spring member integrally formed in one of said portions and axially extending to bear against the other of said portions.

7. The docking station of claim 3, wherein said means to effect axial engagement between said container end surface and exposed timer surface is affixed to at least one of said surfaces.

8. The docking station of claim 7, wherein said means to effect axial engagement between said container end surface and exposed timer surface comprises cooperating mechanical self-engaging surface features.

9. The docking station of claim 7, wherein said means to effect axial engagement between said container end surface and exposed timer surface comprises a layer of contact adhesive.

10. The docking station of claim 1, wherein said platform portion defines a plurality of wells, each well configured to nestingly retain a dispensing container therein and having a different nominal diameter and/or axial length.

11. The docking station of claim 10, wherein said platform portion is disposed for limited relative rotational displacement between first and second end limits of travel with respect to said base portion, whereby an end surface of a first dispensing container disposed in one of said wells is concentrically aligned with a multifunction timer device carried with said base portion when said platform portion is in said first end limit of travel and an end surface of a second dispensing container disposed in another of said wells is concentrically aligned with said multifunction timer device carried with said base portion when said platform portion is in said second end limit of travel.

12. The docking station of claim 11, further comprising a radially elongated indicator integrally formed for movement with said base portion and configured to selectively point toward one of said wells.

13. The docking station of claim 12, wherein said elongated indicator comprises a handle extending upwardly through a circumferentially elongated slot formed in said platform portion.

14. The docking station of claim 11, wherein said scanner is carried for rotational displacement with said base portion, and
    wherein said base portion comprises means operative to positionally register a multifunction timer device with respect to said scanner.

15. The docking station of claim 1, wherein said well is integrally formed with said platform portion.

16. The docking station of claim 1, wherein said well is discretely formed and is releasably affixed to said platform portion.

17. The docking station of claim 1, further comprising at least one generally cylindrical insert adapted for insertion within said well to accept dispensing containers of differing characteristic diameter and/or length.

18. The docking station of claim 1, wherein said well includes a tapered trench extending toward said scanner to expand said field of focus.

19. The docking station of claim 1, wherein said scanner is a bar code scanner.

20. The docking station of claim 11, further comprising locking means operable to selectively, releasably interconnect said platform portion and said base portion to prevent relative rotational displacement there between.

21. A docking station for programming and mounting a multifunction timer device to a dispensing container, said docking station comprising:
    a base portion defining means operative to fixedly preposition a multifunction timer device in alignment with an infrared light emitting diode (LED) for optical coupling there between;
    a platform portion carried on said base portion, said platform portion defining means to nestingly retain an end surface of a dispensing container in substantial axial alignment with an exposed surface of said prepositioned multifunction timer device;
    means to effect engagement between said container end surface and exposed timer surface;
    a scanner having a field of focus directed toward an outer peripheral surface of a dispensing container retained on said platform portion and operable for encoding information imprinted thereon; and a controller adapted for electrically interconnecting said LED and scanner with a host data processing system, said controller operative to write selected data to said multifunction timer device via said LED optical coupling as a function of said encoded information and related data stored in said host data processing system.

22. A method of programming and mounting a multifunction timer device to a dispensing container comprising the steps of:

forming a docking station having, a base portion operative to fixedly support an infrared light emitting diode (LED), said base portion including guide walls forming a pocket for receiving and pre-positioning a multifunction timer device in alignment with said LED for optical coupling there between, a platform portion carried on said base portion, said platform portion defining a well configured to nestingly retain a dispensing container therein in substantial axial alignment with said base portion pocket, said well including guide walls operative to concentrically align and axially position an end surface of a dispensing container disposed therein with an exposed surface of said prepositioned multifunction timer device, means to effect axial engagement between said container end surface and exposed timer surface, a scanner having a field of focus directed toward an outer peripheral surface of a dispensing container positioned within said well and operable for encoding information imprinted thereon, and a controller adapted for electrically interconnecting said LED and scanner;

connecting the docking station with a host data processing system of the type including a CPU, memory, a data entry device and a data display device;

filling a medication dispensing container with a prescribed medication;

preparing a visually discernable information label containing information and data pertaining to the prescription;

applying the label to an outer peripheral surface of the dispensing container;

inserting a multifunction timer device within said base portion pocket;

inserting the dispensing container within said well;

scanning the container label and storing data derived there from in said host data processing system;

writing selected data to said multifunction timer device via said LED optical coupling as a function of said encoded information and related data stored in said host data processing system;

establishing contact of an exposed surface of the multifunction timer device with an end surface of the dispensing container to effect interconnection thereof; and removing the dispensing container and attached multifunction timer device from the docking station.

23. The method of claim 22, further comprising the step of:
displacing the platform portion with respect to the base portion to effect engagement of an exposed surface of the multifunction timer device with an end surface of the dispensing container to effect interconnection thereof.

24. The method of claim 23, further comprising the step of:
releasing the platform portion with respect to the base portion to effect withdrawal of the multifunction timer device from said base portion pocket.

25. The method of claim 22, further comprising the step of:
rotating the dispensing container while disposed within said well to substantially align the label with the scanner.

* * * * *